United States Patent [19]

Shen et al.

[11] 4,061,759

[45] Dec. 6, 1977

[54] ETHENYL AND ETHYNYL MERCAPTOALKYL PYRIDINES

[75] Inventors: Tsung-Ying Shen, Westfield; Howard Jones, Holmdel; Conrad P. Dorn, Plainfield, all of N.J.

[73] Assignee: Merck & Co., Inc., Rahway, N.J.

[21] Appl. No.: 706,033

[22] Filed: July 16, 1976

Related U.S. Application Data

[60] Division of Ser. No. 578,692, May 19, 1975, abandoned, which is a continuation-in-part of Ser. No. 464,011, April 26, 1974, abandoned, which is a continuation-in-part of Ser. No. 368,772, June 15, 1973, abandoned.

[51] Int. Cl.$^2$ .................. C07D 213/32; A61K 31/44
[52] U.S. Cl. ..................... 424/263; 260/294.8 C; 260/294.8 D; 260/294.8 E; 260/294.8 G; 260/294.8 H; 260/294.8 J; 424/250; 542/455
[58] Field of Search .................. 260/294.8 G, 240 D, 260/297 S; 424/263

[56] References Cited

U.S. PATENT DOCUMENTS 3,971,797   7/1976   Shen et al. ..................... 260/294.8 E Primary Examiner—Alan L. Rotman
Attorney, Agent, or Firm—Raymond M. Speer; Frank M. Mahon; William H. Nicholson

[57] ABSTRACT

Mercaptoalkylpyridines carrying an ethenyl or ethynyl substituent are prepared from known pyridine compounds, principally pyridoxine, by known chemical procedures, and are useful in the treatment of rheumatoid arthritis and related inflammatory diseases.

21 Claims, No Drawings

ETHENYL AND ETHYNYL MERCAPTOALKYL PYRIDINES

This is a division of application Ser. No. 578,692, filed, May 19, 1975, now abandoned, which in turn is a continuation-in-part of co-pending application Ser. No. 464,011, filed Apr. 26, 1974, now abandoned, which in turn is a continuation-in-part of application Ser. No. 368,772, filed June 15, 1973, now abandoned.

This invention is concerned with novel mercaptoalkylpyridines and derivatives thereof carrying a nuclear unsaturated substituent, methods for their preparation, a method of treating rheumatoid arthritis and related inflammatory diseases with the novel compounds and pharmaceutical compositions containing these novel compounds as active ingredient.

More particularly, the invention is concerned with novel compounds of structural formula:

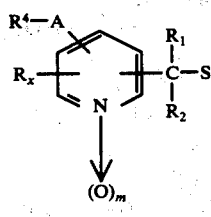

or pharmaceutically acceptable salt thereof, wherein
m is 0 or 1;
X is an integer from 0-3;
A is

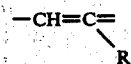

or —C≡C—;
where
$R^7$ is hydrogen, chloro, or fluoro;
$R^1$ and $R^2$ are hydrogen or $C_{1-3}$ alkyl;
$R^3$ is (a) hydrogen, (b) -$SO_3H$, (c) -$PO_3H_2$, (d) amidino, (e) $N(C_{1-4}$ alkyl), (f) -$CH_2CH(NH_2)COOH$, (g) ethoxycarbonylmethyl,

where E represents (1) adamantyl, (2) $C_{3-8}$ cycloalkyl, (3) $C_{1-5}$ alkoxy, (4) $C_{2-6}$ alkyl, (5) $N(C_{1-4}$ alkyl$)_2$, (6) phenyl, (7) 2-acetoxyphenyl, (8) 2-hydroxy-4-(2,4-difluorophenyl)phenyl, (9) 3-chloro-4-allyloxybenzyl, (10) α-methyl-4-isobutylbenzyl, (11) α-methyl-3-phenoxybenzyl, (12) α-methyl-3-benzoylbenzyl, (13) 1-(6-methoxynaphth-2-yl)ethyl, (14) α-methyl-3-fluoro-4-phenylbenzyl, (15) 2-(3-chloro-4-cyclohexylbenzoyl)ethyl, (16) 2-(3-trifluoromethylanilino)phenyl, (17) 2-(2,3-dimethylanilino)phenyl, (18) 2-(2,6-dichloro-3-methylanilino)phenyl, (19) 2-(3-trifluoromethylanilino-3-pyridyl, (20) 2-(2-methyl-3-chloroanilino)-3-pyridyl, or

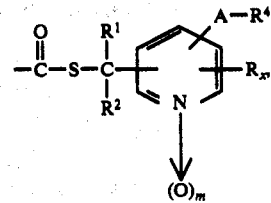

where G represents (1) $C_{1-4}$ alkoxy, (2) -S(alkali metal) or

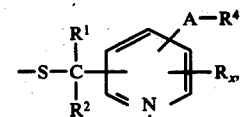

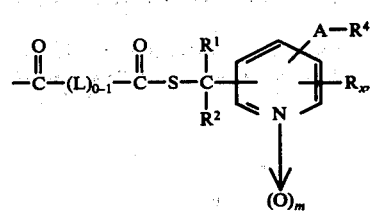

wherein L represents (1) -$(CH_2)_{1-5}$-, (2) phenylene, or

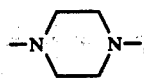

(m) -S-$R^8$, wherein $R^8$ represents (1) -$C(CH_3)_2CH(NH_2)COOH$, (2) $C_{1-5}$ alkyl, (3) $C_{2-5}$ alkenyl, (4) phenyl-$C_{1-3}$alkyl, (5) phenyl, (6) $C_{2-5}$alkynyl, (7) 2-carboxyphenyl, or

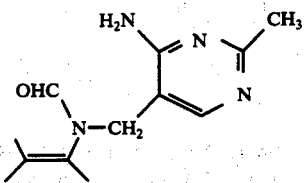

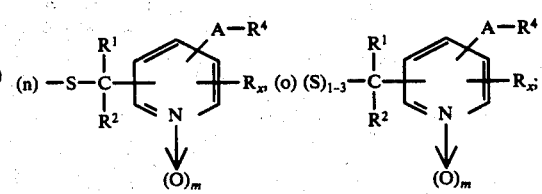

$R^4$ is hydrogen, $C_{1-3}$ alkyl, phenyl, chloro, carboxy, $C_{1-3}$ alkoxycarbonyl, fluoro; and R is (a) $C_{1-3}$ alkyl, (b) hydroxy,

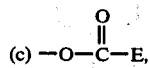

(d) hydroxy-$C_{1-3}$ alkyl; and (e) when one R is hydroxy adjacent to the

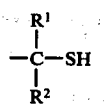

group the oxygen and sulfur thereof may be joined together through a group of formula:

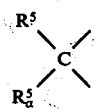

wherein $R^5$ and $R_a^5$ are the same or different and each is hydrogen, $C_{1-6}$ alkyl, phenyl, dimethylphenyl, or difluorofluorophenyl, or taken together, $R^5$ and $R_a^5$ represent =O or =S.

A preferred embodiment of this invention is the compound described above wherein the -AR⁴ group and the

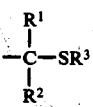

group are alternatively in the 4 and 5-positions of the pyridine ring, X = 2.

A still more preferred embodiment is the compound of structural formula:

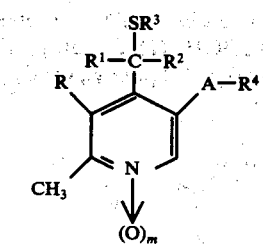

and especially wherein A-R⁴ represents -CH=CH₂, R represents hydroxy or $C_{2-6}$ alkanoyloxy, and $R^3$ represents hydrogen, —SO₃H, $C_{2-6}$ alkanoyl, or

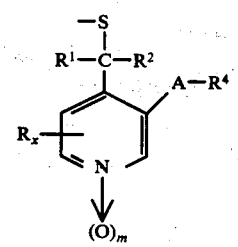

or a pharmaceutically acceptable salt thereof.

Of particular importance are the compounds:
2-methyl-3-hydroxy-4-mercaptomethyl-5-vinylpyridine;
2-methyl-3-acetoxy-4-acetylthiomethyl-5-vinylpyridine;
2-methyl-3-hydroxy-4-acetylthiomethyl-5-vinylpyridine;
2-methyl-3-hydroxy-5-vinylpyrid-4-ylmethylthiosulfuric acid;
3-ethoxycarbonyloxy-4-ethoxycarbonylthiomethyl-2-methyl-5-vinylpyridine; and
bis[2-methyl-3-hydroxy-5-vinylpyrid-4-ylmethyl]disulfide or a pharmaceutically acceptable salt thereof.

In the above descriptions $R^3$ has been defined in part as —SO₃H and —PO₃H₂ to facilitate description. It is understood that molecules within these descriptions actually exist as internal salts, having structures such as

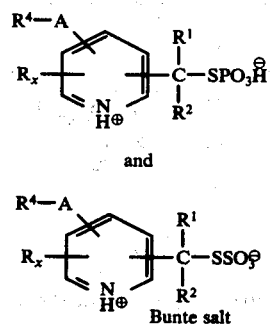

and

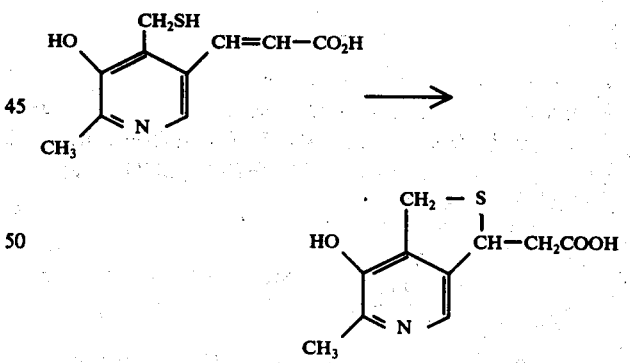

Bunte salt

The Bunte salts as well as having utility against rheumatoid arthritis, are valuable intermediates in the synthesis of the disulfides. Thus, these Bunte salts form another embodiment of this invention. Certain of the other compounds described above can and do exist as isomers and cyclic internal condensation products, for example:

and such cyclic isomers are considered to be within the scope of the invention.

The pharmaceutically acceptable salts include those prepared from mineral and organic acids commonly employed in the pharmaceutical art, such as hydrochloric, hydrobromic, sulfuric, nitric, maleic, fumaric, tartaric, succinic acids, or the like, as well as alkali metal salts of the mercaptans, and the thiophosphoric acid and thiosulfuric acid analogs described above, and divalent metallic complexes.

It is well known in the art that the mercapto group is subject to reaction with aldehydes and ketones to form hemimercaptals and hemimercaptoles. It is similarly known in the art, Field et al., J. Med. Chem. 12, 624–628 (1969) that many of these hemimercaptals and hemimercaptoles prepared from biologically active mercaptans serve as "latentiating" derivatives, or as chemical modifications of biologically active compounds to form new compounds, which upon in vivo enzymatic or chemical transformation will liberate the parent compounds. Latentiation may also provide means of favorably influencing absorption, transport, distribution, localization, metabolism, toxicity, and duration of action. as well as stability. Included with the group of aldehydes and ketones suitable for this purpose are chloral, hexafluoroacetone, acetone, benzaldehyde, pyruvate, and ketomalonate. Since latentiation of mercapto groups by this means is known in the art, these latentiating derivatives are considered to be within the spirit scope of the novel method of treatment and novel compounds of this invention.

Another means of latentiation is by addition of the thiols of this invention to $\alpha,\beta$-unsaturated acids such as maleic acid and cinnamic acid as described by Srivistava et al., in J. Med. Chem., 16, 428–429 (1973).

Latentiation may also be achieved by substitution of the mercapto hydrogen with a 1-methyl-4-nitroimidazol-5-yl group as in azathioprine or a pivaloyloxymethyl group.

In spite of the extensive antiinflammatory research in the past two decades, there is still an obvious need for an effective and well tolerated agent for the treatment of rheumatoid arthritis. Conventional nonsteroidal antiinflammatory-analgesic-antipyretic agents, such as aspirin and many experimental new drugs under clinical evaluation, are mostly effective in providing symptomatic relief of the acute syndrome only. As a consequence, the anti-rheumatic actions of two old remedies, gold and D-penicillamine, in spite of their potential side-effects, have received renewed interest in the past few years. The clinical efficacy of both drugs was reconfirmed by well-controlled multi-center clinical studies. Several rheumatologists have expressed the opinion that a superior D-penicillamine-like compound would be a valuable contribution to medicine in this important field. It is, therefore, an important discovery that the novel mercaptoalkyl pyridines of this invention have an important degree of anti-rheumatoid arthritis activity.

For this purpose the compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal, intraarticular, injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the antiinflammatory agents are employed.

Dosage levels of the order to 0.5 mg. to 140 mg. per kilogram of body weight per day are useful in the treatment of the above-indicated conditions (25 mg. to 7 gms. per patient per day). For example, inflammation is effectively treated and anti-pyretic and analgesic activity manifested by the administration of about .1 to 50 mg. of the compound per kilogram of body weight per day (5 mg. to 3.5 gms. per patient per day). Advantageously, from about 1 mg. to about 15 mg. per kilogram of body weight per daily dosage produces highly effective results (50 mg. to 1 gm. per patient per day).

The amount of active ingredient that may be combined with the carrier materials to produce a single dosage form will vary depending upon the host treated and the particular mode of administration. For example, a formulation intended for the oral administration of humans may contain from 5 mg. to 5 gm. of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The novel compounds of this invention are generally prepared from known pyridine derivatives.

Where the final product has a free α-mercaptoalkyl group in 2, 4, or 6 position and is adjacent an hydroxyl substituent such as in 2-methyl-3-hydroxy-4-mercaptomethyl-5-vinylpyridine, it is readily formed by dissolving the corresponding α-hydroxyalkyl compound in a lower alkanol, preferably ethanol, containing an alkali metal hydroxide, such as sodium hydroxide or potassium hydroxide, treating the solution with carbon disulfide and heating for 2–8 hours at a temperature from 50° C. to reflux, followed by acidification of the cooled mixture. Isolation is accomplished by standard techniques such as concentration to dryness and extraction with a solvent.

An alternative procedure for producing a free α-mercaptoalkyl group irrespective of its location on the pyridine nucleus is the removal of protective groups from a preformed thio compound. For example, S-acyl compounds, such as the S-benzoyl, are converted to the free mercapto by art recognized hydrolytic procedures, for example by saponification with dilute alkali at room temperature to about 75° C.

The mercaptoalkyl group in any position may also be prepared by first converting the corresponding hydroxyalkyl group to the chloromethyl or bromomethyl by heating at 50° C. to reflux temperature for 1–4 hours with thionyl chloride or with concentrated hydrobromic acid respectively. The resulting halo methyl compound is then treated in one of two alternate procedures.

a. The halomethyl compound in aqueous solution is treated with a lower alkyl alkali metal xanthogenate, such as ethyl potassium xanthogenate at 5–10° C. for 1–4 days, and the xanthate product is extracted out with a solvent such as ether and reduced with lithium aluminum hydride or sodium borohydride. Alternatively, the xanthate can be converted to mercapto by heating at 50° C. to reflux with aqueous alcoholic alkali such as sodium or potassium hydroxide.

b. The halomethyl compound is heated in a lower alkanol such as methanol, with thiourea at 50° C. to reflux for 1–4 hours. The isothioureide is then heated at 50° C. to reflux in water or a lower alkanol such as ethanol containing an alkali metal hydroxide such as sodium or potassium hydroxide preferably in an inert atmosphere such as nitrogen. Alternatively, the thioureide may be reduced with lithium aluminum hydride or lithium borohydride as previously described.

The Bunte salts of the mercaptoalkyl compounds of this invention are prepared from the corresponding chloro- or bromomethyl compounds and sodium thiosulfate in aqueous alcohol by warming the mixture at 50° to reflux for a few minutes to about 2 hours.

These Bunte salts, as well as being useful in the novel method of treatment, find utility as an intermediate to the disulfides, both symmetrical and unsymmetrical and also to the free mercaptomethyl compounds.

The mercaptomethyl compounds are obtained from the Bunte salts by reduction with lithium aluminum hydride or sodium borohydride at $-10°$ to $10°$ C. in an inert organic solvent, such as tetrahydrofuran or mixtures of tetrahydrofuran and ether.

Disulfides are obtained from the Bunte salts by mixing at 20°-100° C. approximately molar equivalents of a Bunte salt and a sulfhydryl compound such as penicillamine, an alkylmercaptan, etc., or a mercaptomethyl pyridine of this invention such as 2-methyl-3-hydroxy-4-mercaptomethyl-5-vinylpyridine with an aqueous alkali metal hydroxide such as sodium or potassium hydroxide.

Alternatively, a Bunte salt, such as that of 2-methyl-3-hydroxy-4-mercaptomethyl-5-vinylpyridine, is converted to the symmetrical disulfide such as bis[2-methyl-3-hydroxy-5-vinylpyridyl-4-methyl]disulfide by various procedures: (a) by treating it with aqueous alkali or dilute mineral acid at 20°-100° C.; (b) by treating it with Na$_2$S$_2$ in an aqueous alkanol at 20°-100° C. for 3-24 hours; (c) by treating it with Na$_2$S in an aqueous alkanol at 20°-100° C. for a few minutes to about 4 hours; or (d) by treating it with iodine at ambient temperature in an aqueous alkanol for 8-24 hours.

Another procedure for obtaining symmetrical disulfides such as bis[2-methyl-3-hydroxy-5-vinylpyridyl-4-methyl]disulfide is by treating an hydroxyalkyl compound such as 2-methyl-3-hydroxy-4-hydroxymethylpyridine with phosphorus pentasulfide in a solvent such as pyridine at 50° to reflux temperature for 2-10 hours followed by acidification and further heating for 1-4 hours.

A further procedure for obtaining symmetrical disulfides such as bis[2-methyl-3-hydroxy-5-vinylpyridyl-4-methyl]disulfide is by treating an isothiuronium salt such as 2-methyl-3-hydroxy-5-vinylpyridyl-4-methyl isothiuronium salt at 10° to room temperature with dilute aqueous caustic such as 5-15% (w/v) sodium hydroxide and aqueous hydrogen peroxide for a few minutes to 2 hours.

Similarly, an isothiuronium salt can be converted to a disulfide by substituting sodium tetrathionate in the above reaction, followed by acidification to about pH 5-7.

The alkyl xanthogenates of this invention such as 2-methyl-3-hydroxy-5-vinylpyridyl-4-methyl ethyl xanthogenate are also converted to disulfides by treatment with ammonium hydroxide and slow addition of hydrogen peroxide at 0°-15° C. in aqueous alkanolic solution for 1-5 hours.

An additional procedure for preparing the symmetrical disulfides of this invention such as bis[2-methyl-3-hydroxy-5-vinylpyridyl-4-methyl]disulfide is by treating a compound of formula:

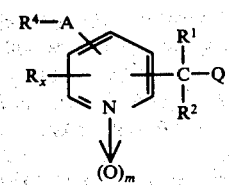

where Q is a facile leaving group such as chloro, bromo, iodo, methanesulfonyloxy, benzenesulfonyloxy, toluenesulfonyloxy, or the like, with sodium sulfide (Na$_2$S$_2$). The reaction is conducted in aqueous alkanol at about room temperature although temperature is not critical for 2-24 hours.

The disulfide dimers may also be prepared from the corresponding monomer xanthate by treating it for 12 hours to 4 days at room temperature with concentrated ammonium hydroxide.

Another method of preparing the disulfide dimers involves oxidation of the corresponding monomer by bubbling air through a solution of the monomer in dilute ammonium hydroxide at 20°-50° C. for 15-30 hours, or in an organic solvent at 20°-50° for periods of 1-4 days.

Alternatively, the monomer may be oxidized with a per-acid such as m-chloroperbenzoic acid, peracetic acid, perphthalic acid, sodium hypochlorite, iodine, or hydrogen peroxide in aqueous solution at about 0°-15° C.

As well as being a final product, a disulfide is frequently employed as a convenient means of protecting the mercapto group while manipulating other functional groups on the molecule. In this event, the monomer is subsequently obtained by reduction. Useful reducing systems are lithium aluminum hydride in ether at room temperature for 1-20 hours; zinc in hydrochloric acid; zinc in acetic acid; or tin in hydrochloric acid.

Another type of derivative found useful both as a final product and as particularly useful protective groups because they tie up both an hydroxyl group and a vicinal hydroxymethyl or mercaptomethyl, are cyclic ketals and acetals. They are prepared by treating, for example, a 3-hydroxy-4-mercaptomethyl compound with a carbonyl compound such as acetone or benzaldehyde saturated with hydrogen chloride at -5° to +5° C. for 2-6 hours.

A typical derivative is:

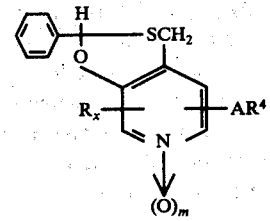

Where the desired product is in the form of its N-oxide, the oxygen must be introduced before the mercapto group, as the latter is subject to oxidation. The N-oxides are usually prepared by treating a pyridine free base with a peracid such as m-chloroperbenzoic acid at room temperature in an inert solvent such as chloroform, or methylene chloride for a period of 16-48 hours.

Another type of cyclic compound are those of structure:

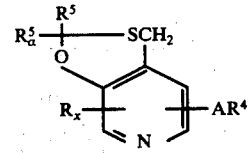

where R$^5$ and R$_a^5$ taken together, represent =O and =S. These cyclic compounds are prepared simply by adding phosgene or thiophosgene in an inert solvent such pyridine benzene, chloroform, tetrahydrofuran, or the like, to a solution of the free mercapto compound in a similar solvent at -5° to +10° C. and then aging at room temperature overnight.

Certain other useful end products are considered as biological equivalents of the mercaptomethyl compounds.

One such is the thiophosphoric acid prepared by treating a chloroalkyl compound with trisodium phosphorothioate in aqueous solution at about 0° C. and aging the mixture for 10–20 hours at 0°–10° C. followed by acidification.

Another type of useful end product is the S-ester or carbamoyl. These are generally formed by treating the mercaptoalkyl compound with an acylating compound such as a carboxylic anhydride or carboxylic chloride or a carbamoyl chloride in an inert organic solvent such as tetrahydrofuran with or without the presence of an acid acceptor such as pyridine or triethylamine or the pyridine nitrogen of the substrate itself. Where the substrate carries a free hydroxyl group as well as the mercaptoalkyl group, it too may become acylated. However, by control of the amount of acylating agent, either the S-acyl or the O,S-diacyl compound can be obtained. The reaction is conducted at room temperature to reflux temperature for 1 hour to 2 days.

Related acylating procedures conducted generally as described above for the normal acylation involves the use of reagents having dual acyl groups such as isophthaloyl chloride, N,N'-dichlorcarbonylpiperazine, phosgene, oxalyl chloride, glutaroyl chloride, succinoyl chloride, or pentane-dicarbonyl chloride, which result in symmetrical dicarbothioates.

Phosgene is also a useful reagent for preparing S-carbamates. By using an excess of phosgene and adding a mercaptoalkylpyridine dropwise followed by evaporation of excess phosgene and treatment with an amino compound such as ammonia or an amino acid ester at room temperature for 3–24 hours.

The compounds, where $R^3$ is

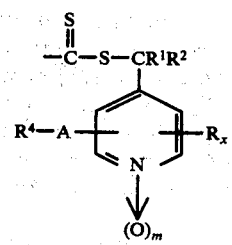

are prepared by treating a chloro- or bromoalkylpyridine with disodium trithiocarbonate in a lower alkanol at 10°–50° C. for 1–6 hours.

Similarly prepared are compounds wherein $R^3$ is

(alkali metal). In this case the solvent is preferably an aqueous alkanol, and an excess of the alkali metal trithiocarbonate is employed. After adjusting the pH to 6.2–6.5 with dilute acid, the product precipitates.

Another type of useful end-product are the sulfenamides of structure:

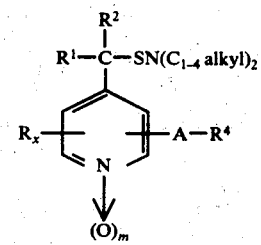

These are prepared by treating the mercaptoalkyl compounds with thiocyanogen in an inert solvent such as ether. The resulting precipitate is then treated with $di(C_{1-4}$ alkyl) amine for ½ to 3 hours.

Related to the previously described disulfides is the disulfide represented by the partial structural formula:

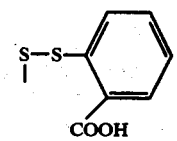

This compound is prepared by treating a mercaptoalkyl compound with o-carboxyphenyl-o-carboxybenzenthiolsulfonate in a lower alkanol for 4–24 hours at 10°–50° C.

An alternative procedure for the preparation of S-acyl compounds is by treatment of a corresponding halomethyl compound with an alkali metal thioacyl compound such as potassium thiobenzoate, in an inert solvent such as an aqueous alkanol at room temperature to about 100° C. for ½ to 3 hours.

Another novel unsymmetrical disulfide is that prepared from the mercaptoalkyl compounds of this invention and thiamine-S-monooxide prepared by suspending the latter in water and adding the former slowly with stirring. After ½ or 3 hours at room temperature to about 50° C., the mixture is filtered, and the product is extracted from the filtrate.

The compounds, wherein $R^3$ is —CH$_2$CO$_2$Et and —CH$_2$CH(NH)CO$_2$H, are prepared by treating a bromo- or chloromethylpyridine with ethyl mercaptoacetate or cysteine respectively in a lower alkanol and in the presence of a strong base such as a sodium alkoxide in sufficient quantity both to react with any acidic functional groups such as a nuclear hydroxyl on the pyridine ring or the carboxyl group of cysteine and to neutralize the HBr or HCl produced in the condensation reaction.

As well as the disulfides described above, polysulfides, particularly the tri- and tetra- sulfides are a further embodiment of this invention. They are prepared by forming an alkali metal salt of the sulfhydryl group by treating one of the mercaptomethyl pyridines of this invention in an aprotic solvent such as dimethyl formamide, dimethyl sulfoxide, or the like, with an alkali metal hydride such as sodium hydride or an alkali organic compound such as n-butyl lithium or sodium phenyl, at −10° C. to +10° C., followed by treatment of the alkali metal sulfide with sulfur dichloride (SCl$_2$) or sulfur monochloride (S$_2$Cl$_2$) for 5–24 hours. The reaction is quenched by addition of water and the trisulfide or tetrasulfide respectively is isolated by extraction.

If the mercaptoalkyl compound in the above reaction carries a free hydroxyl or other functional group that could participate in reaction with the reagents, it is advisable to protect it with a standard blocking group such as benzyl.

The novel compounds of this invention also carry an alkenyl or alkynyl substituent. The alkenyl is generally prepared from the corresponding formylpyridine by means of a standard Wittig reagent, for example, triphenylmethylphosphonium bromide in the presence of a strong base such as sodium hydride in a solvent such as dimethyl sulfoxide. The reaction is best conducted in the cold, below about 25° C. followed by aging at room temperature for prolonged periods such as 1-3 days or by heating at temperatures of 40°-90° C. for 1 to 7 hours.

Where the vinyl substituent carries plural halo substituents, reactions related to the Wittig reaction are employed which involve preparation of the Wittig reagent in situ. For example, the dichlorovinyl and chlorofluorovinyl group are introduced by treating a pyridine aldehyde with a mixture of triphenylphosphine, potassium t-butoxide and chloroform or dichlorofluoromethane at 40°-50° C. for 2-7 hours. The difluorovinyl analog is prepared by treating the pyridinealdehyde with triphenylphosphine and sodium chlorodifluoroacetate in glyme or diglyme at 60°-100° C. for 16-48 hours.

Alternatively, the alkenyl group may be prepared from a formylpyridine by first subjecting it to a Grignard reaction under standard conditions to form an α-hydroxyalkylpyridine followed by thermal dehydration of the -hydroxy compound by refluxing in a high boiling solvent such as diethyleneglycol dimethyl ether (diglyme).

The alkynyl analogs are readily prepared from the corresponding alkenyl compounds by addition of bromine across the double bond by simply adddding bromine dropwise to the alkene in an inert solvent such as chloroform preferably at about 0°-20° C., followed by double dehydrobromination. The dehydrobromination occurs on heating the dibromo compound in alcoholic alkali such as alcoholic potassium hydroxide.

Various other synthetic procedures are employed to prepare pyridine derivatives with the desired substitution to serve as intermediates for final conversion to the mercaptoalkylpyridines of this invention. All of these procedures are well known in the art and available to skilled practitioners. Details of these procedures are provided in the examples that follow for the preparation of specific novel compounds from known starting materials.

EXAMPLE 1

2-Methyl-3-Hydroxy-4 Mercaptomethyl-5-Vinylpyridine Hydrochloride

Step A: Preparation of 3,4α-di-O-isopropylidene derivative of 2-methyl-3-hydroxy-4-hydroxymethyl-5-vinylpyridine 67 Ml. of n-butyl lithium (1.9 M in n-hexane) was run into a stirred suspension of triphenylmethylphosphonium bromide (42.7 g., 0.12 M) at room temperature in tetrahydrofuran (300 ml.) under nitrogen. To this stirred solution a solution of the 3,4α-di-O-isopropylidene derivative of 2-methyl-3-hydroxy-4-hydroxylmethyl-5-formylpyridine (24.7 gm. 0.119 M) in tetrahydrofuran (300 ml.) was added dropwise over 1 hour. The reaction was aged 1 hour at room temperature and the refluxed for 4 hours.

The solution was evaporated to dryness first under house pump vacuum then high vacuum at 30°-50° C. The red-oily product was triturated with 400 ml. ether. Solid triphenylphosphine oxide was filtered off (17.0 gm.) and the ether filtrate was extracted with 2 × 200 ml. saturated sodium bisulfite solution and evaporated to dryness to give a reddish-yellow oil. The product was used as in the next step.

Step B: Preparation of 2-methyl-3-hydroxy-4-hydroxymethyl-5-vinylpyridine hydrochloride A solution of the red oil obtained above (25 gm. 0.122 M) was stirred in 2.5 N hydrochloric acid (500 ml.) and acetone (500 ml.) at reflux under nitrogen for 1.5 hours. The acetone was distilled off to a temperature of 90° and the cooled solution was extracted with ethyl acetate (3 × 400 ml.). The aqueous layer was poured into excess saturated sodium bicarbonate solution (700 ml.).

The aqueous layer was extracted with ethyl acetate (1 × 400 ml.). The organic solution was dried (MgSO$_4$), filtered and evaporated to give an off-white solid recrystallizable from ethyl acetate, m.p. 164°-166°, 9.4 gm.

Step C: Preparation of 2-methyl-3-hydroxy-4-mercaptomethyl-5-vinylpyridine hydrochloride To a 1 liter 3-necked flask equipped with nitrogen inlet tube a thermometer and additional funnel on top of a condenser was added 530 ml. of 90% ethanol and 53.4 gm. of NaOH. After solution was complete, 50 gm. of produce from Step B was added. To the resulting solution (under N$_2$) was added 30 ml. of SC$_2$ dropwise over a period of about ½ hour with stirring at 10°-15°. The resulting mixture was then stirred for ½ hour at 20°, then cooled to about 15° C. and an additional 20 ml. of CS$_2$ was added dropwise and refluxed for 4 hours. The mixture was then cooled to about 10° C. and concentrated HCl was added until the pH remained at 2. (About 80 ml. required). The mixture was kept in an ice bath overnight, and concentrated under reduced pressure (bath temperature 20°) to remove the ethanol. The resulting material was added (N$_2$ atmos) to a cold stirred suspension of 120 gm. of NaHCO$_3$ in 1 liter of water. The organic material was extracted with 3 × 300 ml. of ethyl acetate (air excluded as much as possible). The combined extracts were dried (MgSO$_4$), filtered and concentrated under reduced pressure. The residue was purified by chromatography using about 1 kg. of SiO$_2$ (Baker) and ethyl acetate as the eluant. The appropriate fractions (as determine by tlc-EtOAc dev) were combined and concentrated to an appropriate volume giving the white crystalline free base. 1st crop. m.p. 115°-117° (33 gm). Crop 2, m.p. 114°-116° (6 gm.).

Anal. C$_9$H$_{11}$NOS. Calcd: C, 59.66; H, 6.12; N, 7.73; D, 17.7. Found: C, 59.64; H, 6.35; N, 7.26; S, 17.30.

It was converted to the hydrochloride by the following procedure:

The free base (39 gm.) was dissolved in 500 ml. of dry THF and, with stirring, dry HCl was admitted keeping the temperature below 25° until a slight excess was present. The resulting white precipitate was collected, washed with tetrahydrofuran and dried under vac. m.p. 149°-152°, wt 45 g.

Anal. C$_9$H$_{12}$ClNOS, m.w. 217.7 Calcd: C, 49.65; H, 5.56; N, 6.44; S, 14.73. Found: C, 49.87; H, 5.82; N, 6.44; S, 15.10.

Employing the procedure substantially as described in Example 1, but substituting for the triphenylmethylphosphonium bromide used in Step A thereof, an equivalent amount of triphenylethylphosphonium bromide, triphynelbenzylphosphonium bromide and triphenylchloromethylphosphonium bromide, there are prepared in sequence, respectively, Step A:

3,4α-di-O-isopropylidene derivative of 2-methyl-3-hydroxy-4-hydroxymethyl-5-(1-propenyl)pyridine (oil, 35% yield);

3,4α-di-O-isopropylidene derivative of 2-methyl-3-hydroxy-4-hydroxymethyl-5-styrylpyridine; and 3,4α-di-O-isopropylidene derivative of 2-methyl-3-hydroxy-4-hydroxymethyl-5-(2-chlorovinyl) pyridine.

Step B:

2-methyl-3-hydroxy-4-hydroxymethyl-5-(1-propenyl)-pyridine hydrochloride (100% yield);

2-methyl-3-hydroxy-4-hydroxymethyl-5-styrylpyridine hydrochloride; and 2-methyl-3-hydroxy-4-hydroxymethyl-5-(2-chlorovinyl)pyridine hydrochloride.

Step C:

2-methyl-3-hydroxy-4-mercaptomethyl-5-(1-propenyl)-pyridine hydrochlorine (60% yield, m.p. 175°–178° C);

2-methyl-3-hydroxy-4-mercaptomethyl-5-styrylpyridine hydrochloride (m.p. 190°–195° C.); and 2-methyl-3-hydroxy-4-mercaptomethyl-5-(2-chlorovinyl)pyridine hydrochloride.

EXAMPLE 2

2-Methyl-3-Hydroxy-4-Mercaptomethylpyridine-5-Acrylic Acid Hydrochloride

A mixture of 1.23 g. of 2-methyl-3-hydroxy-4-hydroxymethylpyridine-5-acrylic acid, 1 g. of sodium metal, 5 ml. of carbon disulfide, and 75 ml. of absolute ethanol was refluxed for 26 hours. Concentrated hydrochloric acid (3 ml.) was added and the mixture was evaporated to dryness. The residue was extracted with 125 ml. of boiling ethanol and filtered hot. Evaporation of the extract gave a syrup which was crystallized from chloroform-ether to give 2-methyl-3-hydroxy-4-mercaptomethylpyridine-5-acrylic acid hydrochloride, m.p. 227°–228° C.

EXAMPLE 3

2-Methyl-3-Hydroxy-4-Vinyl-5-Benzoylthimethylpyridine

Step A: Preparation of 3,4α-di-O-isopropylidene derivative of 2-methyl-3-hydroxy-4-hydroxymethyl-5-benzoylthiomethylpyridine To a stirred solution of 80 g. of the 3,4α-di-O-isopropylidene derivative of 2-methyl-3-hydroxy-4-hydroxymethyl-5-chloromethylpyridine in 1 liter of ethanol under nitrogen there was added 96 g. of potassium thiobenzoate in 200 ml. of water over 30 minutes. After 1 hour, the ethanol was evaporated at 40° C. and the aqueous solution was extracted with 4 × 300 ml. of ethyl acetate. The extract was washed with 1 × 75 ml. of water, dried over magnisium sulfate and concentrated to dryness to give 116 g. of 3,4α-di-O-isopropylidene derivative of 2-methyl-3-hydroxy-4-hydroxymethyl-5-benzoylthiomethylpyridine, m.p. 74°–77° C.

Step B: Preparation of 2-methyl-3-hydroxy-4-hydroxymethyl-5-benzoylthiomethylpyridine The product from Step A was dissolved in 1 liter of ethanol and was treated with 1 liter of 2.5 N hydrochloric acid. The mixture was heated on a steam bath for 30 minutes. The ethanol was evaporated at 60° C. and the aqueous solution was poured into excess sodium bicarbonate solution. The precipitate was collected and dried to give 48 g. of 2methyl-3-hydroxy-4-hydroxymethyl-5-benzoylthiomethylpyridine, m.p. 174°–177° C.

Step C: Preparation of 2-methyl-3-hydroxy-4-formyl-5-benzoylthiomethylpyridine

A solution of the 10 g. of the product from Step B in 300 ml. of hot chloroform was treated with 100 g. of maganese dioxide. After ½ hour of stirring, the mixture was filtered and the filtrate was evaporated to dryness to give 9.2 g. of 2-methyl-3-hydroxy-4-formyl-5-benzoylthiomethylpyrididne, m.p. 127°–130° C.

Step D: Preparation of 2-methyl-3-acetoxy-4-formyl-5-benzoylthiomethylpyridine

A mixture of 11 g. of product from Step C, 4.62 g. of acetic anhydride, 4.62 g. of triethylamine, and 30 ml. of dry tetrahydrofuran was aged at room temperature for 1.5 hours and evaporated at 20° to a small volume. The residue was diluted with ethyl acetate, washed with water, dried over magnesium sulfate, and evaporated to dryness to give 12.3 g. of 2-methyl-3-acetoxy-4-formyl-5-benzoylthiomethylpyridine, m.p. 128°–130° C. (dec.).

Step E: Preparation of 2-methyl-3-acetoxy-4-(1-hydroxyethyl)-5-benzoylthiomethylpyridine To a stirred suspension of the aldehyde (6.58 g.) in tetrahydrofuran (200 ml.), methyl magnesium bromide (0.02 mole; 6 ml. of 3.6 M in tetrahydrofuran) (6.6 ml.) was added dropwise and the mixture was stirred overnight at room temperature. The reaction mixture was poured into 500 ml. of an ice-water solution of ammonium chloride (100 gm.), stirred for a few minutes and extracted well with ether (4 × 300 ml.). The combined extracts were washed with water, dried over magnesium sulfate, filtered and evaporated to give an oil which was used directly in the next step.

Step F: Preparation of 2-methyl-3-hydroxy-4-vinyl-5-benzoylthiomethylpyridine

The product from Step E (2 gm.) was added to diglyme and refluxed 3 hours. The mixture was evaporated to dryness to give 2-methyl-3-hydroxy-4-vinyl-5-benzoylthiomethylpyridine. This material was purified by chromatography on 800 gm. of silica gel by elution with 10% methanol in chloroform (v/v).

EXAMPLE 4

2-Methyl-3-Hydroxy-4-Vinyl-5-Mercaptomethylpyridine

A mixture of 1 g. of 2-methyl-3-hydroxy-4-vinyl-5-benzoylthiomethylpyridine, 10 ml. of tetrahydrofuran and 10 ml. of 2.5 N aqueous sodium hydroxide was aged at room temperature overnight. The solution was acidified to about pH 6 with hydrochloric acid and then adjusted to pH 7.5 with solid sodium bicarbonate. The mixture was extracted with 3 × 100 ml. of ethyl acetate:isopropanol (9:1 v/v). The extract was dried over magnesium sulfate and concentrated to an oil which crystallized on trituration with ether to give 175 mg. of 2-methyl-3-hydroxy-4-vinyl-5-mercaptomethyl-pyridine, m.p. 130°-140° C.

EXAMPLE 5

2-Methyl-3-Hydroxy-4-Acetylthiomethyl-5-Vinylpyridine

A mixture of 2.54 g. of 2-methyl-3-hydroxy-4-mercaptomethyl-5-vinylpyridine hydrochloride, 120 ml. of anhydrous tetrahydrofuran, 3.82 ml. of triethylamine, and 1.32 ml. of acetic anhydride was aged overnight at room temperature. After evaporating to dryness, the residue was dissolved in ethyl acetate, extracted with aqueous sodium bicarbonate solution, dried over magnesium sulfate, and evaporated to dryness. After trituration with ether, the residue crystallized to give 0.8 g. of 2-methyl-3-hydroxy-4-acetylthiomethyl-5-vinylpyridine, m.p. 130°-132° C.

EXAMPLE 6

2-Methyl-3-Acetoxy-4-Acetylthiomethyl-5-Vinylpyridine

A mixture of 680 mg. of acetic anhydride and 10 ml. of tetrahydrofuran was added slowly to 653 mg. of 2-methyl-3-hydroxy-4-mercaptomethyl-5-vinylpyridine in 20 ml. of tetrahydrofuran at 10° C. After stirring for one hour at room temperature, the mixture was evaporated to dryness. The residue was triturated with a mixture of 20 ml. of ethyl acetate and 20 ml. of water. The ethyl acetate was separated, dried over magnesium sulfate, and evaporated to dryness. The residue was recrystallized from cyclohexane to give 2-methyl-3-acetoxy-4-acetylthiomethyl-5-vinylpyridine, m.p. 72°-73° C. The same product is obtained by starting with the S-acetate product of Example 5.

EXAMPLE 7

3-O-4α-S-Benzylidene Derivative of 2-Methyl-3-Hydroxy-4-Mercaptomethyl-5-Vinylpyridine 2-Methyl-3-hydroxy-4-mercaptomethyl-5-vinylpyridine (1 g.) was dissolved in tetrahydrofuran and stirred at 0° C. with 900 mg. of benzaldehyde while gaseous hydrogen chloride was introduced over a 2 hour period. After aging overnight at room temperature, the mixture was evaporated to dryness. The residue was taken up in water and poured onto excess solid sodium bicarbonate and extracted with ethyl acetate. The extract was dried and evaporated to dryness, and the residue was chromatographed on silica gel by elution with tetrahydrofuran to give 220 mg. of 3-O-4α-S-benzylidene derivative of 2-methyl-3-hydroxy-4-mercaptomethyl-5-vinylpyridine (oil).

Similarly prepared were the 3-O-4α-S-(2,4-difluorobenzylidine), 3,O-4α-S-(2,4-dimethylbenzylidine), and 3-O-4α-S-isopropylidine derivatives of 2-methyl-3-hydroxy-4-mercaptomethyl-5-vinylpyridine.

EXAMPLE 8

Ethylcarbonates of 2-Methyl-3-Hydroxy-4-Mercaptomethyl-5-Vinylpyridine

A solution of 1.1 g. of 2-methyl-3-hydroxy-4-mercaptomethyl-5-vinylpyridine in 50 ml. of dry tetrahydrofuran and 10 ml. of dry pyridine was stirred at room temperature and ethylchloroformate (20% excess) in 10 ml. of tetrahydrofuran was added over 10 minutes. After 1 hour the solution was evaporated to about 5 ml. and diluted with 100 ml. of ethyl acetate and extracted with water. The organic layer was dried and concentrated to dryness and chromatographed on silica gel by elution with 1:1 (v/v) ether-hexane to give, after conversion to the hydrochloride salt:
2-methyl-3-ethoxycarbonyloxy-4-ethoxycarbonylthiomethyl-5-vinylpyridine.HCl, m.p. 142°-145° C.; and
2-methyl-3-hydroxy-4-ethoxycarbonylthiomethyl-5-vinylpyridine.HCl.

Following the procedure of Example 8 but substituting for the ethylchloroformate used therein, equivalent amounts of adamantanoyl chloride, cyclopropylcarbonyl chloride, 2-acetoxysalicyloyl chloride, benzoyl chloride, 2-hydroxy-4-(2,3-difluorophenyl)benzoyl chloride, 3-chloro-4-allyloxyphenylacetyl chloride, α-methyl-4-isobutylphenylacetyl chloride, α-methyl-3-phenoxyphenylacetyl chloride, α-methyl-3-benzoylphenylacetyl chloride, α-methyl-6-methoxynaphth-2-ylacetyl chloride, α-methyl-3-fluoro-4-phenylphenylacetyl chloride, 4-(3-chloro-4-cyclohexylphenyl)-4-ketobutyryl chloride, 2-(3-trifluoromethylanilino)benzoyl chloride, 2-(2,3-dimethylanilino)benzoyl chloride, 2-(2,6-dichloro-3-methylanilino)benzoyl chloride, 2-(3-trifluoromethylanilino)nicotinoyl chloride, 2-(2-methyl-3-chloroanilino)nicotinoyl chloride, there are produced respectively the S-mono and O,S-di- adamantanoyl, cyclopropanoyl, 2-acetoxybenzoyl, benzoyl, 2-hydroxy-4-(2,4-difluorophenyl)benzoyl, 3-chloro-4-allyloxyphenylacetyl, α-methyl-4-isobutylphenylacetyl, α-methyl-3-phenoxyphenylacetyl, α-methyl-3-benzoylphenylacetyl, α-methyl-6-methoxynaphth-2-ylacetyl, α-methyl-3-fluoro-4-phenylphenylacetyl, 4 (3-chloro-4-cyclohexylphenyl)-4-ketobutyryl, 2-(3-trifluoromethylanilino)benzoyl, 2-(2,3-dimethylanilino)benzoyl, 2-(2,6-dichloro-3-methylanilino)benzoyl, 2-(3-trifluoromethylanilino)-nicotinoyl, 2-(2-methyl-3-chloroanilino)nicotinoyl derivatives of 2-methyl-3-hydroxy-4-mercaptomethyl-5-vinylpyridine.

Following the procedure of Example 8 but substituting for the 2-methyl-3-hydroxy-4-mercaptomethyl-5-vinylpyridine used therein an equivalent amount of 2-methyl-3-hydroxy-4-mercaptomethyl-5-ethynylpyridine (Example 9) there are produced:
2-methyl-3-ethoxycarbonyloxy-4-ethoxycarbonylthiomethyl-5-ethynylpyridine;
2-methyl-3-hydroxy-4-ethoxycarbonylthiomethyl-5-ethynylpyridine;
2-methyl-3-adamantanoyloxy-4-adamantanoylthiomethyl-5-ethynylpyridine;
2-methyl-3-hydroxy-4-adamantanoylthiomethyl-5-ethynylpyridine;
2-methyl-3-cyclopropanoyloxy-4-cyclopropanoylthiomethyl-5-ethynylpyridine;
2-methyl-3-hydroxy-4-cyclopropanoylthiomethyl-5-ethynylpyridine;

2-methyl-3-(2-acetoxybenzoyloxy)-4-acetoxybenzoyl-thiomethyl)-5-ethynylpyridine;
2-methyl-3-hydroxy-4-(2-acetoxybenzoylthiomethyl)-5-ethynylpyridine.

EXAMPLE 9

2-Methyl-3-Hydroxy-4-Mercaptomethyl-5-Ethynylpyridine Hydrochloride

Step A: Preparation of 2-methyl-3-hydroxy-4-hydroxymethyl-5-(1,2-dibromoethyl)pyridine Bromine (320 mg.) was added over 10 minutes to a stirred suspension of 320 mg. of 2-methyl-3-hydroxy-4-hydroxymethyl-5-vinylpyridine in chloroform at 10° C. After stirring 10 minutes, the mixture was evaporated to an oil.

Step B: Preparation of 2-methyl-3-hydroxy-4-hydroxymethyl-5-ethynylpyridine

The oily product from Step A was refluxed in 15 ml. of 10% (w/v) ethanolic potassium hydroxide under nitrogen for 10 minutes. After cooling the solvent was evaporated. The residue was extracted with 2 × 20 ml. of hot isopropanol which was then filtered and evaporated to give solid 2-methyl-3-hydroxy-4-hydroxymethyl-5-ethynylpyridine, m.p. 170°–171° C.

Step C: Preparation of 2-methyl-3-hydroxy-4-mercaptomethyl-5-ethynylpyridine hydrochloride The product from Step B (3.26 g.) was treated with 1.6 g. of sodium hydroxide and 3 ml. of carbon disulfide according to the procedure described in Example 1, Step C, to give 2-methyl-3-hydroxy-4-mercaptomethyl-5-ethynylpyridine hydrochloride, m.p. 114°–126° C. (dec.).

EXAMPLE 10

2-Methyl-3-Hydroxy-4-(1-mercaptoethyl)-5-Vinylpyridine

Step A: Preparation of 2-methyl-3-hydroxy-4-formyl-5-vinylpyridine

A solution of 10 g. of 2-methyl-3-hydroxy-4-hydroxymethyl-5-vinylpyridine in 300 ml. of hot chloroform was treated with 100 g. of manganese dioxide. After ½ hour of stirring, the mixture was filtered and the filtrate was evaporated to dryness to give 2-methyl-3-hydroxy-4-formyl-5-vinylpyridine.

Step B: Preparation of 2-methyl-3-hydroxy-4-(1-hydroxyethyl)-5-vinylpyridine To a stirred suspension of the aldehyde (0.2 mole) in tetrahydrofuran (200 ml.), methyl magnesium chloride (0.44 mole; 3.35 M in tetrahydrofuran) (13.2 ml.) was added dropwise and the mixture was stirred overnight at room temperature. The reaction mixture was poured into 500 ml. of an ice-water solution of ammonium chloride (100 gm.), stirred for a few minutes and extracted well with ether (4 × 300 ml.). The combined extracts were washed with water, dried over magnesium sulfate, filtered and evaporated to give an oil which was used directly in the next step.

Step C: Preparation of 2-methyl-3-hydroxy-4-(1-mercaptoethyl)-5-vinylpyridine Prepared by the procedure of Example 1, Step C, to yield 2-methyl-3-hydroxy-4-(1-mercaptoethyl)-5-vinylpyridine.

EXAMPLE 11

2-Methyl-3-Hydroxy-4-(2-mercaptobut-2-yl)-5-Vinylpyridine

Step A: Preparation of 2-methyl-3-hydroxy-4-acetyl-5-vinylpyridine

To 750 ml. of dry methylene chloride containing 47.5 ml. of dry pyridine was added with stirring and cooling 29.6 g. of chromium trioxide. The mixture was aged 20 minutes at room temperature and then treated with a solution of 10.96 g. of the product from Example 10, Step B, in 250 ml. of dry methylene chloride over 15 minutes. After one hour at room temperature, the reaction mixture was filtered and the residue was washed with 2 × 100 ml. of methylene chloride. The methylene chloride filtrates were extracted with 3 × 500 ml. of 5% (w/w) aqueous sodium hydroxide solution, dried over magnesium sulfate and evaporated to dryness. The residue was crystallized from hexane to give 2-methyl-3-hydroxy-4-acetyl-5-vinylpyridine.

Step B: Preparation of 2-methyl-3-hydroxy-4-(2-hydroxybut-2-yl)-5-vinylpyridine A solution of 3.93 g. of the product from Step A in 200 ml. of tetrahydrofuran was treated dropwise with 110% excess of ethyl magnesium bromide in tetrahydrofuran. After aging 2 days at ambient temperature the reaction was quenched on ice-water (100 ml.) containing 10 g. of ammonium chloride. The aqueous layer was separated and extracted with ether. The combined organic layers were dried over magnesium sulfate and evaporated to dryness to give 2-methyl-3-hydroxy-4-(2-hydroxybut-2-yl)-5-vinylpyridine, which was used directly in the next step.

Step C: Preparation of 2-methyl-3-hydroxy-4-(2-mercaptobut-2-yl)-5-vinylpyridine Prepared by the procedure of Example 1, Step C, to yield 2-methyl-3-hydroxy-4-(2-mercaptobut-2-yl)-5-vinylpyridine.

EXAMPLE 12

2-Vinyl-3-Hydroxy-4-Mercaptomethyl-5-Hydroxymethylpyridine

Step A: Preparation of ethyl α-formyl-α-formamidoacetate diethylacetal

A solution of ethyl α-formyl-α-formamido acetate (1 equivalent) in 200 ml. anhydrous ethanol is saturated with dry hydrogen chloride at 0° C. The solution is allowed to reach room temperature and is aged for 16 hours. The solution is then concentrated under reduced pressure to yield the desired acetal as an oil.

Step B: Preparation of 4-formyl-5-ethoxyoxazole diethyl acetal

A 2 liter flask is charged with 340 ml. anhydrous chloroform and 142 gm. phosphorus pentoxide. To this stirred mixture, a solution of 0.5 mole ethyl α-formyl-α-formamidoacetate diethyl acetal in 200 ml. chloroform is added over 10 minutes. The reaction is then maintained under gentle reflux for 6 hours. To the cooled reaction mixture is added 750 ml. 20% potassium hydroxide solution with good agitation over 1.5 hours. After addition is complete, aging is continued for 30–60 minutes at room temperature. The layers are separated, and the aqueous phase is extracted with fresh chloroform (2 × 200 ml.). The combined chloroform extracts are dried over anhydrous magnesium sulfate. After solvent removal, the residual oil is distilled at reduced pressure to afford the desired oxazole.

Step C: Preparation of diethyl 2-formyl-3-hydroxypyridine-4,5-dicarboxylate diethyl acetal A mixture of 31 gm. (0.2 m) diethyl maleate and 0.1 m of oxazole from Step A is charged to a flask and heated to 110°–115° C. for 4 hours. The mixture is cooled and 20 ml. of a 25% solution of dry hydrogen chloride in absolute ethanol is added. Then 300 ml. ether is introduced and after cooling overnight, the crystalline hydrochloride is isolated. The corresponding free base is obtained by introducing the hydrochloride into excess aqueous sodium bicarbonate, followed by chloroform extraction. The chloroform extracts, after magnesium sulfate drying, are concentrated at reduced pressure affording the desired free base.

Step D: Preparation of 2-formyl-3-hydroxy-4,5-dihydroxymethylpyridine hydrochloride A flask is charged with 1.14 gm. (0.03 m) lithium aluminum hydride and 50 ml. anhydrous ether. After cooling a solution of 0.01 m. of the diester from Step C in 5 ml. ether is added dropwise with stirring. The reaction mixture is then maintained under gentle reflux for 6 hours. Then the reaction mixture is cooled, and 100 ml. ice-water added dropwise with stirring, Then carbon dioxide gas is introduced for 30 minutes. The resulting solid is collected by filtration, and stirred with 100 ml. aqueous ethanol (1:1). Carbon dioxide gas is again introduced for 30 minutes. After filtration, the solids are washed with hot ethanol (3 × 50 ml.). All filtrates and washings are combined, acidified with hydrochloric acid, warmed for 30 minutes at 50° C, and evaporated to dryness at reduced pressure. Extraction of the residue with hot ethanol (4 × 25 ml.), followed by filtration and evaporation, gives the crude dicarbinol.

Step E: Preparation of 2-formyl-3-acetoxy-4-acetoxymethyl-5-acetoxymethypyridine A solution of one equivalent of 2-formyl-3-hydroxy-4,5-dihydroxymethylpyridine hydrochloride in 400 ml. anhydrous tetrahydrofuran is treated with four equivalents of triethylamine and aged for one hour at room temperature. Then three equivalents of acetic anhydride are introduced, and the reaction mixture is aged 4 hours at room temperature. The reaction mixture is concentrated under reduced pressure to a gum. This is treated with a mixture of 300 ml. of diethyl ether and 300 ml. of distilled water. After shaking well, the layers are separated and the ether layer is dried over magnesium sulfate. After evaporation to dryness, the desired triacetate is obtained as a viscous oil.

Step F: Preparation of 2-vinyl-3-hydroxy-4,5-dihydroxymethylpyridine hydrochloride A 2 liter flask is charged with one equivalent of methyl triphenylphosphonium chloride and 600 ml. of anhydrous diethyl ether. This solution is cooled to 0° C. and one equivalent of n-butyllithium in hexane is introduced over a 30 minute period under nitrogen. When addition is complete, the solution is aged an additional 30 minutes at 0°–5° C. Then a solution of one equivalent of 2-formyl-3-acetoxy-4,5-diacetoxymethyl pyridine in 250 ml. of anhydrous ether is added dropwise with stirring over a one hour period. The reaction mixture is then aged 16 hours at room temperature, and is then cooled to 0° C. and filtered. The filtrate is concentrated to dryness under reduced pressure and treated with a mixture of 500 ml. of 2.5 N hydrochloric acid and 300 ml. of ethyl acetate. After shaking well, the organic phase is separated and discarded. The aqueous phase is extracted with 2 more 300 ml. portions of ethyl acetate and these too are discarded. The aqueous phase is then refluxed with stirring under nitrogen for 3 hours and after cooling is poured onto excess aqueous sodium bicarbonate. The crude, solid, free base is isolated by filtration and air dried. This crude solid is taken up into 300 ml. dry tetrahydrofuran and saturated with dry hydrogen chloride at 0° C. Then 300 ml. dry diethyl ether is introduced and the desired hydrochloride crystallized. It is isolated by filration and dried in vacuo.

Step G: Preparation of 2-vinyl-3-hydroxy-4-mercaptomethyl-5-hydroxymethylpyridine The product from Step F is treated with sodium hydroxide and carbon disulfide as described in Example 1, Step C, to produce 2-vinyl-3-hydroxy-4-mercaptomethyl-5-hydroxymethylpyridine.

EXAMPLE 13

2-Methyl-3-Hydroxy-4-Mercaptomethyl-5-Hydroxymethyl-6-Vinylpyridine

Step A: Preparation of N-acryloylalanine ethyl ester

To 0.5 moles of alanine ethyl ester hydrochloride in 500 ml. of benzene is added 0.5 moles of acryloyl chloride. To this stirred mixture is added portionwise 0.6 moles of anhydrous sodium carbonate. The reaction mixture is then refluxed for 1 hour, stirred and additional 2 hours, filtered, and the filtrate concentrated to give N-acryloylalanine ethyl ester.

Step B: Preparation of 5-ethoxy-4-methyl-2-vinyloxazole

To a suspension of 1.0 mole of phosphorus pentoxide in 300 ml. of dry chloroform is added dropwise with stirring a solution of 0.5 mole of N-acryloylalanine ethyl ester. The reaction mixture is heated at gentle reflux for 5 hours and then cooled. To the cooled mixture is added with rapid stirring 750 ml. of 20% aqueous potassium hydroxide. After stirring at room temperature for 1 hour, the chloroform layer is separated and the aqueous layer extracted with 2 × 200 ml. of chloroform. The combined chloroform extracts are washed with water, dried over sodium sulfate, and concentrated in vacuo to yield 5-ethoxy-4-methyl-2-vinyloxazole.

Step C: Preparation of dimethyl 2-methyl-3-hydroxy-6-vinylpyridine 4,5-dicarboxylate A mixture of 0.2 mole of dimethyl maleate and 0.1 mole of 5-ethoxy-4-methyl-2-vinyloxazole are heated at 110°–115° C. for 4 hours. The reaction mixture is cooled and 20 ml. of a 25% solution of hydrogen chloride (dry) in absolute methanol added. Addition of ether to the cooled reaction mixture precipitates the hydrochloride salt of the product. The free base is obtained by dissolving the hydrochloride salt in a minimum volume of water, adding solid sodium bicarbonate to pH 6.5 to 7.0 and extracting with chloroform. The combined chloroform extracts are dried over sodium sulfate and concentrated in vacuo to give dimethyl 2-methyl-3-hydroxy-6-vinylpyridine 4,5-dicarboxylate.

Step D: Preparation of 2-methyl-3-hydroxy-4,5-di(hydroxymethyl)-6-vinylpyridine To a suspension of 0.15 moles of lithium aluminum hydride in 250 ml. of ether is added dropwise with stirring a solution of 0.05 moles of dimethyl 2-methyl-3-hydroxy-6-vinylpyridine 4,5-dicarboxylate in 150 ml. of ether. The mixture is refluxed for 6 hours and stirred overnight at room temperature. The reaction mixture is cooled and 100 ml. of water added dropwise with stirring. The resulting mixture is saturated with carbon dioxide for 30 minutes and then filtered. The precipitate is stirred with 250 ml. of ethanol-water (1:1) and saturated again with carbon dioxide and filtered. The solid is then extracted twice with 100 ml. of boiling ethanol. The combined filtrates are evaporated to dryness in vacuo. The residue is extracted 5 times with 100 ml. of boiling ethanol. The combined extracts are filtered and evaporated to dryness to give 2-methyl-3-hydroxy-4,5-di(hydroxymethyl)-6-vinylpyridine.

Step E: Preparation of 2-methyl-3-hydroxy-4-mercaptomethyl-5-hydroxymethyl-6-vinylpyridine Treatment of the product of Step D with sodium hydroxide and carbon disulfide by the procedure described in Example 1, Step C, yields 2-methyl-3-hydroxy-4-mercaptomethyl-5-hydroxymethyl-6-vinylpyridine.

EXAMPLE 14

Bunte salt of 2-methyl-3-hydroxy-4-mercaptomethyl-5-vinylpyridine

Step A: Preparation of 2-methyl-3-hydroxy-4-chloromethyl-5-vinyl pyridine hydrochloride A mixture of 1.65 g. of 2-methyl-3-hydroxy-4-hydroxymethyl-5-vinylpyridine hydrochloride, 1 ml. of thionyl chloride and 20 ml. of tetrahydrofuran is refluxed 6 hours. After cooling, the precipitate is collected on a filter, washed with ether and dried to give 2-methyl-3-hydroxy-4-chloromethyl-5-vinyl pyridine hydrochloride.

Step B: Preparation of Bunte salt of 2-methyl-3-hydroxy-4-mercaptomethyl-5-vinylpyridine A solution of 20 g. of sodium thiosulfate pentahydrate in 15 ml. of water is added to a solution of 18 g. of 2-methyl-3-hydroxy-4-chloromethyl-5-vinylpyridine hydrochloride in 100 ml. of 50% ethanol. The mixture is heated 1 hour at 75° C., cooled and evaporated to dryness to give Bunte salt of 2-methyl-3-hydroxy-4-mercaptomethyl-5-vinylpyridine, m.p. 198°–200° C.

EXAMPLE 15

2-Methyl-3-Hydroxy-4-Mercaptomethyl-5-Vinylpyridine Mixed Disulfide with penicillamine, Dihydrochloride The Bunte salt (0.01 mole) from Example 14, 0.01 mole of penicillamine and 3 molecular equivalents of sodium hydroxide (2.5 N aqueous solution) are warmed together on a steam bath for 2 hours. After cooling the mixture is extracted with 2 × 50 ml. of ethyl acetate. The extract is dried over magnesium sulfate and concentrated to dryness. The residue is taken up in tetrahydrofuran and treated with hydrogen chloride to precipitate 2-methyl-3-hydroxy-4-mercaptomethyl-5-vinylpyridine mixed disulfide with penicillamine, dihydrochloride.

EXAMPLE 16

2-Methyl-3-Hydroxy-5-Vinyl-4-Pyridylmethylthiophosphonic Acid

Step A: Preparation of sodium 2-methyl-3-hydroxy-5-vinyl-4-pyridylmethylthiophosphorothioate Trisodium phosphorothioate (1.8 g., 0.01 mole) in water (5 ml.) is run into a solution of 2-methyl-3-hydroxy-4-chloromethyl-5-vinylpyridine hydrochloride (0.01 mole) in water (15 ml.) at 0°. The solution is stirred overnight at 10°. The solution is diluted with methanol and the solid sodium 2-methyl-3-hydroxy-5-vinyl-4-pyridylmethylthiophosphorothioate is filtered off.

Step B: Preparation of 2-methyl-3-hydroxy-5-vinyl-4-pyridylmethylthiophosphonic acid The product from Step A (0.01 mole) in water (40 ml.) is acidified to pH 1 with dilute hydrochloric acid, and kept there for 20 minutes. Methanol is added to precipitate the subject compound as an internal salt.

EXAMPLE 17

2-Methyl-4-Mercaptomethyl-5-Vinylpyridine

Step A: Preparation of 2-methyl-4-acetoxymethyl-5-hydroxymethylpyridine

2-Methyl-4,5-di(hydroxymethyl)pyridine (0.1 mole) is stirred in pyridine (50 ml.) with acetic anhydride (0.1 mole) at room temperature overnight. The pyridine is evaporated and the residue is dissolved in 10 ml. water and extracted with 2 × 30 ml. of chloroform. After drying over magnesium sulfate, the chloroform is evaporated and the residue is chromatographed on a silica gel column using benzene-ethanol as eluate. By this procedure is obtained:
1. 2-methyl-4-acetoxy-5-hydroxymethylpyridine;
2. 2-methyl-4-hydroxymethyl-5-acetoxymethylpyridine;
3. 2-methyl-4,5-di(acetoxymethyl)pyridine.

Step B: Preparation of 2-methyl-4-acetoxymethyl-5-formylpyridine

This product is prepared by oxidation of 2-methyl-4-acetoxymethyl-5-hydroxymethylpyridine (from Step A) with chromium trioxide in pyridine by the procedure substantially as described in Example 11, Step A.

Step C: Preparation of 2-methyl-4-acetoxy-5-vinylpyridine

This product is prepared from the product of Step B by means of a Wittig reaction employing triphenylmethylphosphorium bromide as reagent and the procedure substantially as described in Example 1, Step A.

Step D: Preparation of 2-methyl-4-hydroxymethyl-5-vinylpyridine

The product from Step C (0.05 mole) is stirred in aqueous alcoholic solution (1:1) of 2.5 N sodium hydroxide (40 ml.) at room temperature for 4 hours. The mixture is concentrated to dryness. The residue is dissolved in 20 ml. of water, acidified with acetic acid and neutralized with sodium bicarbonate. The precipitate is collected and dried to give 2-methyl-4-hydroxymethyl-5-vinylpyridine.

Step E: Preparation of 2-methyl-4-mercaptomethyl-5-vinylpyridine

The above product, 0.1 mole, is dissolved in 100 ml. of tetrahydrofuran and 0.1 mole of thionyl chloride introduced. After 3 hours reflux, the reaction mixture is cooled and the desired 4-chloromethyl intermediate is isolated by filtration.

The 4-chloromethyl compound (0.1 mole) in 100 ml. of absolute ethanol is added dropwise to a solution of 0.35 equivalents potassium ethylxanthate in 200 ml. of water at 0°-5° C., at such a rate that the temperature does not exceed 10° C. After addition, the reaction is aged one hour at 5°-10° C. and 4 hours at room temperature. The reaction mixture is quenched on 150 ml. of ether and shaken well. After separation, the ether layer is dried over magnesium sulfate and evaporated in vacuo to afford 4-ethylxanthatomethyl intermediate.

The xanthate in 200 ml. of tetrahydrofuran:ether (3:1 v/v) is added to excess lithium aluminum hydride under ether and nitrogen at 0° C. over 30 minutes. After stirring one hour at room temperature, it is poured into a mixture of tetrahydrofuran and saturated ammonium chloride solution. The water layer is separated and extracted with 2 × 400 ml. of tetrahydrofuran. The combined tetrahydrofuran solutions are dried and evaporated to dryness to give 2-methyl-4-mercaptomethyl-5-vinylpyridine.

EXAMPLE 18

2-Methyl-4-Vinyl-5-Mercaptomethylpyridine

Employing the procedure substantially as described in Example 17, Steps B, C, D, E, but substituting for the 2-methyl-4-acetoxymethyl-5-hydroxymethylpyridine used in Example 17, Step B, an equivalent amount of 2-methyl-4-hydroxymethyl-5-acetoxymethylpyridine, there are produced sequentially,
2-methyl-4-formyl-5-acetoxymethylpyridine,
2-methyl-4-vinyl-5-acetoxymethylpyridine,
2-methyl-4-vinyl-5-hydroxymethylpyridine, and
2-methyl-4-vinyl-5-mercaptomethylpyridine.

EXAMPLE 19

2-Vinyl-5-Mercaptomethylpyridine

Step A: Preparation of methyl-6-methylnicotinate

6-Methylnicotinic acid (0.1 mole) is refluxed in 100 ml. of methanol saturated with gaseous hydrogen chloride for 1 hour and then evaporated to dryness. The residue is stirred saturated aqueous sodium bicarbonate solution and the product is extracted into chloroform. The chloroform extract is dried and concentrated to dryness to give methyl 6-methylnicotinate.

Step B: Preparation of 2-methyl-5-hydroxymethylpyridine

Methyl 6-methylnicotinate (0.05 mole) is stirred in dry tetrahydrofuran (50 ml.) at 10° C. while solid lithium aluminum hydride (0.0125 mole) is added over 1 hour. Water (10 ml.) is added with stirring, and the mixture is concentrated to dryness. The residue is extracted several times with hot isopropanol and the combined extracts are filtered and concentrated to dryness to give 2-methyl-5-hydroxymethylpyridine.

Step C: Preparation of 2-methyl-5-acetoxymethylpyridine

2-Methyl-5-hydroxymethylpyridine (0.1 mole) is stirred in pyridine (50 ml.) with acetic anhydride (0.15) mole) at room temperature overnight. The mixture is concentrated to dryness, and the residue is dissolved in 70 ml. of water and extracted with 3 × 25 ml. of chloroform. After drying over magnesium sulfate, the chloroform is concentrated to dryness to give 2-methyl-5-acetoxymethylpyridine.

Step D: Preparation of 2-methyl-5-acetoxymethylpyridine-N-oxide

2-Methyl-5-acetoxymethylpyridine (0.05 mole) is stirred in 50 ml. of chloroform at 15° C. while chloroperbenzoic acid (0.06 mole) is added over 10 min. The solution is extracted with saturated sodium bicarbonate solution (3 × 20 ml.) and 2 × 20 ml. of water. The chloroform is dried over magnesium sulfate, and concentrated to dryness to give 2-methyl-5-acetoxymethylpyridine-N-oxide.

Step E: Preparation of 2,5-di(acetoxymethyl)pyridine

2-Methyl-5-acetoxymethylpyridine-N-oxide (0.05 mole) is refluxed in 50 ml. of acetic anhydride for two hours and then evaporated to dryness. The residue is fractionally distilled under high vacuum to obtain 2,5-di(acetoxymethyl)pyridine.

Step F: Preparation of 2,5-di(hydroxymethyl)pyridine 2,5-Di(acetoxymethyl)pyridine (0.05 mole) is reduced with lithium aluminum hydride (0.025 mole) in tetrahydrofuran (50 ml.) at 0° C. with stirring. After one hour, water is added to decompose excess hydride, and the mixture is concentrated to dryness. The residue is extracted with hot isopropanol (2 × 60 ml.) and the extract is concentrated to dryness to give 2,5-di(hydroxymethyl) pyridine.

Step G: Preparation of 2-formyl-5-hydroxymethylpyridine 2,5-Di(hydroxymethyl)pyridine (10 g.) in 300 ml. of hot chloroform is treated with 100 g. of manganese dioxide. After ½ hour of stirring, the mixture is filtered and the filtrate is evaporated to dryness to give 2-formyl-5-hydroxymethylpyridine.

Step H: Preparation of 2-formyl-5-chloromethylpyridine hydrochloride

2-Formyl-5-hydroxymethylpyridine (0.1 mole) in 100 ml. of tetrahydrofuran is treated with 0.11 mole of thionyl chloride, and the mixture is refluxed 3 hours. The product, 2-formyl-5-chloromethylpyridine hydrochloride is collected by filtration from the cooled reaction mixture.

Step I: Preparation of 2-di(methoxy)methyl-5-chloromethylpyridine hydrochloride A mixture of 0.1 mole of 2-formyl-5-chloromethyl pyridine hydrochloride and 250 ml. of methanol which has been saturated with hydrogen chloride is stirred overnight at room temperature. The reaction rixture is then concentrated in vacuo to give 5-chloromethyl-2-di(methoxy)methylpyridine hydrochloride.

Step J: Preparation of bis[2-formyl-5-pyridylmethyl]disulfide

A solution of 0.1 mole of 2-di(methoxy)methyl-5-chloromethylpyridine in absolute alcohol (150 ml.) is added dropwise at 10°-15° C. over 20 minutes, to a suspension of 6 g. of sodium sulfide ($Na_2S_2$) in 50 ml. of absolute alcohol. The mixture stirred at room temperature for ½ hour, then 15 min. at 40°-50° C. and poured into 800 ml. of water. The mixture is extracted with ether and the extract is dried over magnesium sulfate and concentrated to an oil. The oil is dissolved in 80 ml. of 1 N hydrochloric acid and heated for 2- min. at 40° C. The mixture is cooled, adjusted to pH 7 with sodium bicarbonate and extracted with ethylacetate. The extract is dried over magnesium sulfate and concentrated to dryness to give bis[2-formyl-5-pyridylmethyl]disulfide.

Step K: Preparation of bis[2-vinyl-5-pyridylmethyl]disulfide

Employing the process of Example 1, Step A, using as starting materials bis[2-formyl-5-pyridylmethyl]disulfide and triphenylmethylphosphonium bromide, there is produced bis[2-vinyl-5-pyridylmethyl]disulfide.

Step L: Preparation of 2-Vinyl-5-mercaptomethylpyridine

To a suspension of 0.2 gm. of lithium aluminum hydride in 100 ml. of dry tetrahydrofuran was added 0.004 mole of bis[2-vinyl-5-pyridylmethyl]disulfide. The reaction mixture was stirred for 3 hours at 0°-5°. At this time there was added to the reaction mixture 100 ml. of benzene, 50 ml. of water, and 20 gm. ammonium chloride. The organic layer was separated and the aqueous extracted 2 times with 50 ml. of benzene. The combined benzene extracts were washed well with water, dried over sodium sulfate, and concentrated in vacuo. Chromatography on silica gel (250 gm.) and elution with ether gave 2-vinyl-5-mercaptomethylpyridine.

EXAMPLE 20

2-Methyl-3-Hydroxy-4-Mercaptomethyl-5-Vinylpyridine-N-Oxide Hydrochloride

Step A: Preparation of 3,4α-di-O-isopropylidene derivative of pyridoxine N-oxide The 3,4α-di-O-isopropylidene derivative of pyridoxine (0.05 mole) is stirred in 50 ml. of chloroform at 15° C. while m-chloroperbenzoic acid (0.06 mole) is added over 10 minutes. The solution is extracted with saturated sodium bicarbonate solution (3 + 20 ml.) and water (2 × 20 ml.). The chloroform is dried over magnesium sulfate and concentrated to dryness to give 3,4α-di-O-isopropylidene derivative of pyridoxine N-oxide.

Step B: Preparation of 3,4α-di-O-isopropylidene derivative of Z-methyl-3-hydroxy-4-hydroxymethylpyridine-5-aldehyde-N-oxide To 75 ml. of dry methylene chloride containing 4.75 ml. of dry pyridine is added with stirring and cooling 2.96 g. of chromium trioxide. The mixture is aged 20 minutes at room temperature and then treated with a solution of 1 g. of the product from Step A in 25 ml. of dry methylene chloride over 15 minutes. After one hour at room temperature, the mixture is filtered, and the residue washed with 2 × 10 ml. of methylene chloride. The combined filtrates are extracted with 3 × 50 ml. of 5% (w/v) aqueous sodium hydroxide solution, dried over magnesium sulfate and evaporated to dryness to give 3,4α-di-O-isopropylidene derivative of 2-methyl-3-hydroxy-4-hydroxymethylpyridine-5-aldehyde-N-oxide.

Step C: Preparation of 2-methyl-3-hydroxy-4-mercaptomethyl-5-vinylpyridine-N-oxide hydrochloride By the procedure of Example 1, Steps A, B, and C, using as starting material 3,4α-di-O-isopropylidene derivative of 2-methyl-3-hydroxy-4-hydroxymethylpyridine-5-aldehyde-N-oxide and triphenylmethylphosphonium bromide, there is produced in sequence:

3,4α-di-O-isopropylidene derivative of 2-methyl-3-hydroxy-4-hydroxymethyl-5-vinylpyridine-N-oxide, 2-methyl-3-hydroxy-4-hydroxymethyl-5-vinylpyridine-N-oxide hydrochloride, and 2-methyl-3-hydroxy-4-mercaptomethyl-5-vinylpyridine-N-oxide hydrochloride.

EXAMPLE 21

Bis[2-methyl-3-hydroxy-5-vinyl-4-pyridylmethyl]disulfide

2-Methyl-3-hydroxy-4-mercaptomethyl-5-vinylpyridine hydrochloride (9 g.) is dissolved in 50 ml. water and treated with 2 N ammonium hydroxide to about pH 9. Air is bubbled through the solution for 24 hours. The precipitated bis[2-methyl-3-hydroxy-5-vinyl-4-pyridylmethyl]disulfide is collected on a filter and dried, m.p. 178°-180° (dec.).

EXAMPLE 22

Bis[2-methyl-3-hydroxy-5-vinyl-4-pyridylmethyl]disulfide

2-Methyl-3-hydroxy-4-mercaptomethyl-5-vinylpyridine hydrochloride (4.36 g.) was dissolved in 40 ml. of water at 2°-7° C. under a nitrogen atmosphere. To this solution there was added 2.0 ml. of 30% hydrogen peroxide over 2 mins. while maintaining the temperature at 2°-7° C. After 30 mins. stirring at this temperature, the mixture was filtered and, under nitrogen, the filtrate was stirred with excess saturated sodium bicarbonate solution at 2° C. for 10 minutes. The mixture was filtered quickly and the filter cake was washed with 2 × 40 ml. of acetonitrile. The solids were dried over phosphorus pentoxide to give 1.5 g. of bis[2-methyl-3- hydroxy-5-vinyl-4-pyridylmethyl]disulfide, m.p. >300°. The monohydrate has m.p. 178°–180° C.

EXAMPLE 23

2-Methyl-3-Hydroxy-4-Mercaptomethyl-5-Vinylpyridine

Step A: Preparation of 2-methyl-3-hydroxy-4-benzoylthiomethyl-5-vinylpyridine

To a stirred solution of 65 g. of 2-methyl-3-hydroxy-4-chloromethyl-5-vinylpyridine in 1 liter of ethanol under nitrogen there was added 96 g. of potassium thiobenzoate in 200 ml. of water over 30 minutes. After 1 hour, the ethanol was evaporated at 40° C. and the aqueous solution was extracted with 4 × 300 ml. of ethyl acetate. The extract was washed with 1 × 75 ml. of water, dried over magnesium sulfate and concentrated to dryness to give 2-methyl-3-hydroxy-4-benzoylthiomethyl-5-vinylpyridine.

Step B: Preparation of 2-methyl-3-hydroxy-4-mercaptomethyl-5-vinylpyridine

A mixture of 1 g. of 2-methyl-3-hydroxy-4-benzoylthiomethyl-5-vinylpyridine, 10 ml. of tetrahydrofuran, and 10 ml. of 2.5 N aqueous sodium hydroxide was aged at room temperature overnight. The solution was acidified to about pH 6 with hydrochloric acid and then adjusted to pH 7.5 with solid sodium bicarbonate. The mixture was extracted with 3 × 100 ml. of ethyl acetate: isopropanol (9:1 v/v). The extract was dried over magnesium sulfate and concentrated to give 2-methyl-3-hydroxy-4-mercaptomethyl-5-vinylpyridine.

EXAMPLE 24

2-Methyl-3-Hydroxy-4-Mercaptomethyl-5-Vinylpyridine

2-Methyl-3-hydroxy-4-hydroxymethyl-5-vinylpyridine, 0.1 mole, is dissolved in 100 ml. of tetrahydrofuran and 0.1 mole of thionyl chloride introduced. After 3 hours reflux, the reaction mixture is cooled and the desired 4-chloromethyl intermediate is isolated by filtration.

The 4-chloromethyl compound (0.1 mole) in 100 ml. of absolute ethanol is added dropwise to a solution of 0.35 equivalents potassium ethylxanthate in 200 ml. of water at 0°–5° C., at such a rate that the temperature does not exceed 10° C. After addition, the reaction is aged one hour at 5°–10° C. and 4 hours at room temperature. The reaction mixture is quenched on 150 ml. of ether and shaken well. After separation, the ether layer is dried over magnesium sulfate and evaporated in vacuo to afford 4-ethylxanthatomethyl intermediate.

The xanthate in 200 ml. of tetrahydrofuran:ether (3:1 v/v) is added to excess lithium aluminum hydride under ether and nitrogen at 0° C. over 30 minutes. After stirring one hour at room temperature, it is poured into a mixture of tetrahydrofuran and saturated ammonium chloride solution. The water layer is separated and extracted with 2 × 400 ml. of tetrahydrofuran. The combined tetrahydrofuran solutions are dried and evaporated to dryness to give 2-methyl-3-hydroxy-4-mercaptomethyl-5-vinylpyridine.

EXAMPLE 25

2-Methyl-3-Hydroxy-4-Mercaptomethyl-5-Vinylpyridine Hydrochloride

Step A: Preparation of 2-methyl-3-hydroxy-4-isothioureidomethyl-5-vinylpyridine

A mixture of 21.0 g. of 2-methyl-3-hydroxy-4-chloromethyl-5-vinylpyridine, 6.74 g. of thiourea, and 200 ml. of ethanol was refluxed 3 hours. The cooled mixture was filtered and the solids were washed with ether to give 2-methyl-3-hydroxy-4-isothioureidomethyl-5-vinylpyridine hydrochloride.

Step B: Preparation of 2-methyl-3-hydroxy-4-mercaptomethyl-5-vinylpyridine hydrochloride A mixture of 9.0 g. of the isothioureido compound of Step A, and 60 ml. of 6.5% (w/v) potassium hydroxide was refluxed 4 hours. A black solid was filtered off, and the filtrate was acidified with acetic acid and evaporated to dryness. The residue was extracted with 40 ml. of water and 200 ml. of ether. The aqueous phase was separated, acidified with concentrated hydrochloric acid, basified with sodium bicarbonate solution and extracted with ethyl acetate. Evaporation to dryness gave 2-methyl-3-hydroxy-4-mercaptomethyl-5-vinylpyridine hydrochloride.

EXAMPLE 26

2-Methyl-3-Hydroxy-4-Mercaptomethyl-5-Vinylpyridine

The isothioureido compound from Example 25, Step A, (0.1 mole) in 200 ml. of tetrahydrofuran:ether (3:1 v/v) is added to excess lithium aluminum hydride under ether and nitrogen at 0° C. over 30 minutes. After stirring one hour at room temperature, it is poured into a mixture of tetrahydrofuran and saturated ammonium chloride solution. The water layer is separated and extracted with 2 × 400 ml. of tetrahydrofuran. The combined tetrahydrofuran solutions are dried and evaporated to dryness to give 2-methyl-3-hydroxy-4-mercaptomethyl-5-vinylpyridine.

EXAMPLE 27

2-Methyl-3-Hydroxy-4-Mercaptomethyl-5-Vinylpyridine

The Bunte salt of 2-methyl-3-hydroxy-4-mercaptomethyl-5-vinylpyridine (0.1 mole) in 200 ml. of tetrahydrofuran:ether (3:1 v/v) is added to excess lithium aluminum hydride under ether and nitrogen at 0° C. over 30 minutes. After stirring one hour at room temperature, it is poured into a mixture of tetrahydrofuran and saturated ammonium chloride solution. The water layer is separated and extracted with 2 × 400 ml. of tetrahydrofuran. The combined tetrahydrofuran solutions are dried and evaporated to dryness to give 2-methyl-3-hydroxy-4-mercaptomethyl-5-vinylpyridine.

EXAMPLE 28

Bis[2-methyl-3-hydroxy-5-vinyl-4-pyridylmethyl]Disulfide

The xanthate product (0.05 mole) from Example 24 in 50 ml. of concentrated ammonium hydroxide and 100 ml. of ethanol is stirred overnight at room temperature. The oily residue is extracted into 2 × 100 ml. of methylene chloride and dried over magnesium sulfate. The solution is filtered and treated with dry gaseous hydrogen chloride at 0° C. The precipitate is collected on a filter and dried to give bis[2-methyl-3-hydroxy-5-vinyl-4-pyridylmethyl]disulfide, dihydrochloride.

EXAMPLE 29

Bis[2-Methyl-3-Hydroxy-5-Vinyl-4-Pyridylmethyl]Disulfide Dihydrochloride

The Bunte salt of 2-methyl-3-hydroxy-4-mercaptomethyl-5-vinylpyridine (0.1 mole) was refluxed 18 hours with 1 N sulfuric acid. This was concentrated to dryness, the residue was taken up in isopropanol, filtered, and again evaporated to an oil. The oil was treated with aqueous sodium bicarbonate solution. The resulting solid was collected, dissolved in isopropanol and treated with gaseous hydrogen chloride. Addition of ether caused crystallization of bis[2-methyl-3-hydroxy-5-vinyl-4-pyridylmethyl]disulfide dihydrochloride.

EXAMPLE 30

2-Methyl-3-Hydroxy-4-Mercaptomethyl-5-Vinylpyridine

To a suspension of 0.2 gm. of lithium aluminum hydride in 100 ml. of dry tetrahydrofuran was added 0.004 mole of bis[2-methyl-3-hydroxy-5-vinyl-4-pyridylmethyl]-disulfide. The reaction mixture was stirred for 3 hours at 0°–5°. At this time there was added to the reaction mixture 100 ml. of benzene, 50 ml. of water, and 20 gm. ammonium chloride. The organic layer was separated and the aqueous extracted 2 times with 50 ml. of benzene. The combined benzene extracts were washed well with water, dried over sodium sulfate, and concentrated in vacuo. Chromatography on silica gel (250 gm.) and elution with ether gave 2-methyl-3-hydroxy-4-mercaptomethyl-5-vinylpyridine.

EXAMPLE 31 o-Carboxyphenyl 2-methyl-3-hydroxy-5-vinylpyridin-4-yl-methyl Disulfide

To a solution of 0.02 moles of o-carboxyphenyl o-carboxybenzenethiolsulfonate in 200 ml. of 95% ethanol is added 0.02 moles of fine powdered 2-methyl-3-hydroxy-4-mercaptomethyl-5-vinylpyridine. The reaction mixture is stirred overnight at room temperature and the resulting precipitate filtered to yield o-carboxyphenyl 2-methyl-3-hydroxy-5-vinylpyridin-4-ylmethyl disulfide.

Similarly prepared is o-carboxyphenyl 2-methyl-3-hydroxy-5-ethynylpyridin-4-ylmethyl disulfide.

EXAMPLE 32

S,S′-bis(2-methyl-3-hydroxy-5-vinyl-4-pyridylmethyl)-carbonodithioate Dihydrochloride To an ice cooled solution of 4.5 gm. of 2-methyl-3-hydroxy-4-mercaptomethyl-5-vinylpyridine in 50 ml. of dry pyridine is added dropwise 10 ml. of a 12.5% solution of phosgene is benzene. The reaction mixture is allowed to come to room temperature and stirred for three hours after which time it is concentrated in vacuo. The residue is extracted between benzene and saturated sodium bicarbonate solution. The benzene layer is separated, washed with water, dried over sodium sulfate and concentrated in vacuo. The residue is chromatographed on 250 gm. of silica gel. Elution with ether gives S,S′-bis(2-methyl-3-hydroxy-5-vinyl-4-pyridylmethyl)carbonodithioate dihydrochloride.

Similarly prepared is S,S′-bis(2-methyl-3-hydroxy-5-ethynyl-4-pyridylmethyl)carbonodithioate dihydrochloride.

EXAMPLE 33

S,S′-bis(2-methyl-3-hydroxy-5-vinyl-4-pyridylmethyl) 1,3-benzenedicarbothioate

To a solution of 4.5 gm. (0.02 mole) of 2-methyl-3-hydroxy-4-mercaptomethyl-5-vinylpyridine in 50 ml. of pyridine and 50 ml. of chloroform is added dropwise with stirring a solution of 2.0 gm. (0.01 mole) of isophthaloyl dichloride in 50 ml. of chloroform. The reaction mixture is stirred overnight at room temperature and then concentrated in vacuo. The residue is extracted between benzene and saturated sodium bicarbonate solution. The benzene layer is separated, washed with water, dried over sodium sulfate and concentrated in vacuo to give an oil. Chromatography on 1,000 gm. of silica gel and elution with ether affords S,S′-bis(2-methyl-3-hydroxy-5-vinyl-4-pyridylmethyl) 1,3-benzenedicarbothioate.

Similarly prepared is S,S′-bis(2-methyl-3-hydroxy-5-ethynyl-4-pyridylmethyl) 1,3-benzenedicarbothioate.

EXAMPLE 34

Ethyl N-(2-methyl-3-hydroxy-5-vinyl-4-pyridylmethylthiocarbonyl)glycinate

To a well stirred mixture of 20 ml. of 12.5% phosgene in benzene and 50 ml. of benzene is added dropwise a solution of 2.5 gm. (0.01 moles) of 2-methyl-3-hydroxy-4-mercaptomethyl-5-vinylpyridine in 25 ml. of benzene. The reaction mixture is stirred for 3 hours and then purged with nitrogen for 1 hour to remove any unreacted phosgene. The reaction mixture is then concentrated in vacuo to give a gummy solid. To the above is added 5.6 gm. (0.04 moles) of ethyl glycinate and 100 ml. of dry dioxane. The mixture is stirred and 6 ml. of triethylamine added. After stirring overnight at room temperature, the mixture is concentrated in vacuo and the residue extracted between ether and saturated sodium bicarbonate solution. The ether layer is separated, washed with water, dried over sodium sulfate and concentrated to give crude product. Chromatography on 900 gm. of silica gel and elution with ether gives ethyl N-(2-methyl-3-hydroxy-5-vinyl-4-pyridylmethylthiocarbonyl)-glycinate.

Similarly prepared is ethyl N-(2-methyl-3-hydroxy-5-ethynyl-4-pyridylmethylthiocarbonyl)glycinate.

EXAMPLE 35

N,N′-Diethyl 2-methyl-3-hydroxy-5-vinylpyridin-4-yl-methylsulfenamide

To a suspension of 9.5 gm. of lead thiocyanate in 200 ml. of dry ether which had been cooled to 0°–5°, is added dropwise 3.7 gm. of bromine dissolved in 25 ml. of carbon tetrachloride. The reaction mixture is stirred for 30 minutes after the addition is complete. The supernatant containing the thiocyanogen is decanted into a 1 liter flask equipped with a mechanical stirrer and ether is added to make 500 ml. of solution. A solution of 4.5 gm. of 2-methyl-3-hydroxy-4-mercaptomethyl-5-vinylpyridine in 50 ml. of ether is added dropwise. A heavy precipitate forms immediately and the reaction mixture is stirred for 30 minutes after the addition is complete. Diethylamine (15 ml.) is then added and the reaction mixture allowed to come to room temperature. After 1 hour 200 ml. of benzene and 250 ml. of saturated sodium bicarbonate are added. The organic layer is separated, washed with water, dried over sodium sulfate and concentrated to give an oil. Chromatography on 600 gm. of silica gel and elution with 50% ether in petroleum ether gives N,N'-diethy. 2-methyl-3-hydroxy-5-vinylpyridin-4-ylmethylsulfenamide as an oil.

Similarly prepared is N,N-diethyl 2-methyl-3-hydroxy-5-ethynylpyridin-4-ylmethylsulfenamide.

EXAMPLE 36

4-Dimethylaminocarbonylthiomethyl-3-Hydroxy-2-Methyl-5-Vinylpyridine

To a mixture of 7.4 gm. (0.04 m) of 2-methyl-3-hydroxy-4-mercaptomethyl-5-vinylpyridine in 50 ml. dry pyridine and 50 ml. of chloroform is added dropwise with stirring a solution of 3.25 gm. (0.3 m) of dimethylcarbamoyl chloride in 50 ml. of chloroform.

The reaction mixture is stirred for 3 hours after the addition is completed, then concentrated in vacuo. The residue is extracted between ether-benzene 1:1 and saturated sodium bicarbonate solution. The organic phase is separated, washed well with water, dried over sodium sulfate, and concentrated in vacuo to give crude material. Chromatography on 900 gm. of silica gel gives 4-dimethylaminocarbonylthiomethyl-3-hydroxy-2-methyl-5-vinylpyridine.

Similarly prepared is 4-dimethylaminocarbonylthiomethyl-3-hydroxy-2-methyl-5-ethynylpyridine.

EXAMPLE 37

S,S'-Bis(2-methyl-3-hydroxy-5-vinyl-4-4-pyridylmethyl) 1,4-piperazinedicarbothioate Dihydrochloride To a solution of 4.50 gm. (0.02 m) of 2-methyl-3-hydroxy-4-mercaptomethyl-5-vinylpyridine in 50 ml. of pyridine and 50 ml. of chloroform is added all at once as a solid 2.1 gm. (0.01 m) of N,N'-dichlorocarbonyl piperazine. The reaction mixture is then stirred at room temperature for 4 hours, concentrated in vacuo and extracted between chloroform and saturated sodium bicarbonate solution. The aqueous layer is separated and extracted two times with chloroform. The combined chloroform extracts are washed with water, dried and concentrated to an oil which gradually crystallizes. Recrystallization from methanol gives S,S'-bis(2-methyl-3-hydroxy-5-vinyl-4-pyridylmethyl) 1,4-piperazinedicarbothioate dihydrochloride.

Similarly prepared is S,S'-bis(2-methyl-3-hydroxy-5-ethynyl-4-pyridylmethyl) 1,4-piperazinedicarbothioate dihydrochloride.

EXAMPLE 38

2-Methyl-3-Hydroxy-4-Carbamoylthiomethyl-5-Vinylpyridine

Employing the procedure of Example 34 but substituting for the ethyl glycinate used therein, an equivalent amount of ammonia, there is produced 2-methyl-3-hydroxy-4-carbamoylthiomethyl-5-vinylpyridine.

EXAMPLE 39

2-Methyl-3-Hydroxy-4-Mercaptomethyl-5-(2,2-dichlorovinyl)pyridine Hydrochloride

Step A: Preparation of 5-(2,2-dichlorovinyl)-2,2,8-trimethyl-4H-1,3-dioxino[4,5-c]pyridine To a well stirred ice-cooled mixture of 0.1 mole of triphenylphosphine and 0.1 mole of potassium t-butoxide in 250 ml. of heptane is added over thirty minutes a mixture of 0.1 mole of chloroform in 200 ml. of haptane. The resulting mixture is concentrated in vacuo at 15°-20° to a volume of about 100 ml. and a solution of 0.1 mole of 2,2,8-trimethyl-4H-1,3-dioxino[4,5-c]pyridine-5-carboxaldehyde in 250 ml. of heptane is added. The reaction mixture was heated at 40°-50° for 5 hours, then cooled, filtered, and concentrated in vacuo to give crude product. Chromatography on silica gel and elution with ether-petroleum ether (10-50%) gives pure 5-(2,2-dichlorovinyl)-2,2,8-trimethyl-4H-1,3-dioxino-[4,5-c]pyridine.

Step B: Preparation of 2-methyl-3-hydroxy-4-mercaptomethyl-5-(2,2-dichlorovinyl)pyridine hydrochloride Employing the procedure of Example 1, Steps B and C, for hydrolysis of the isopropylidene group and formation of the mercapto group, there is produced 2-methyl-3-hydroxy-4-mercaptomethyl-5-(2,2-dichlorovinyl)-pyridine hydrochloride.

When dichlorofluoromethane is used in place of chloroform in Step A of the above procedure, there is obtained 5-(2-chloro-2-fluorovinyl)-2,2,8-trimethyl-4H-1,3-dioxino[4,5-c]pyridine, which upon hydrolysis and treatment with carbon disulfide as in Step B, there is produced 2-methyl-3-hydroxy-4-mercaptomethyl-5-(2-chloro-2-fluorovinyl)pyridine hydrochloride.

EXAMPLE 40

2-Methyl-3-Hydroxy-4-Mercaptomethyl-5-(2,2-difluorovinyl)pyridine Hydrochloride

Step A: Preparation of 5-(2,2-difluorovinyl)-2,2,8-trimethyl-4H-1,3-dioxino[4,5-c]pyridine A mixture of 0.1 mole of 2,2,8-trimethyl-4H-1,3-dioxino[4,5-c]pyridine-5-carboxaldehyde, 0.11 mole of triphenylphosphine and 0.11 mole of sodium chlorodifluoroacetate in 100 ml. of diglyme is heated under nitrogen at 90° for 24 hours. The reaction mixture is then filtered and concentrated in vacuo. Chromatography of the residue on silica gel and elution with etherpetroleum ether (10–50%) gives 5-(2,2-difluorovinyl)-2,2,8-trimethyl-4H-1,3-dioxino[4,5-c]pyridine.

Step B: Preparation of 2-methyl-3-hydroxy-4-mercaptomethyl-5-(2,2-difluorovinyl)pyridine hydrochloride Employing the procedure of Example 1, Steps B and C, for hydrolysis of the isopropylidene group and formation of the mercapto group, there is produced 2-methyl-3-hydroxy-4-mercaptomethyl-5-(2,2-difluorovinyl)pyridine hydrochloride.

EXAMPLE 41

Preparation of the compound of formula:

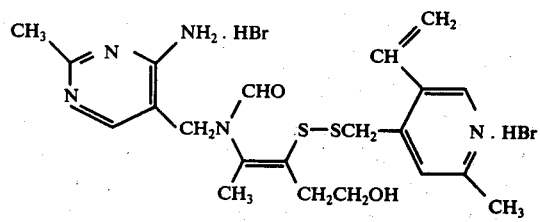

Thiamine-S-monooxide is suspended in 120 ml. of water 1.83 g. of 2-methyl-3-hydroxy-4-mercaptomethyl-5-vinylpyridine is added over 5 min. After stirring for 1 hour, the mixture is filtered and the filtrate is extracted with n-butanol. The extract is washed with water and dried over magnesium sulfate. The dried solution is acidified with 48% hydrobromic acid in acetic acid, and evaporated to dryness. The residue is recrystallized from ethanol to give the desired product.

EXAMPLE 42

Preparation of Mixed Disulfides

Employing the procedure of Example 15, but substituting for the penicillamine used therein, an equivalent amount of ethylmercaptan, allylmercaptan, benzylmercaptan, and thiophenol, there is produced respectively (2-methyl-3-hydroxy-5-vinylpyridyl-4-methyl) (ethyl)disulfide, (2-methyl-3-hydroxy-5-vinylpyridyl-4-methyl) (allyl)disulfide, (2-methyl-3-hydroxy-5-vinylpyridyl-4-methyl) (benzyl)disulfide, and (2-methyl-3-hydroxy-5-vinylpyridyl-4-methyl) (phenyl)disulfide.

EXAMPLE 43

8-Methyl-2-Oxo-5-Vinyl-4H-1,3-Thioxino[4,5-c]Pyridine

To a mixture of 0.01 mole of 2-methyl-3-hydroxy-4-mercaptomethyl-5-vinylpyridine in 50 ml. chloroform and 50 ml. pyridine is added at 0° to 5° a solution of 0.022 moles of phosgene in benzene. The reaction mixture is allowed to warm to room temperature and is stirred overnight. The reaction mixture is then concentrated in vacuo and excess saturated sodium bicarbonate solution is added. The resulting solid is collected by filtration. Chromatography on silica gel and elution with methanol in chloroform (1-5%) gives 8-methyl-2-oxy-5-vinyl-4H-1,3-thioxion[4,5-c]pyridine.

When thiophosgene is used in place of phosgene in the above example, 8-methyl-2-thiono-4H-1,3-dioxino[4,5-c]pyridine is obtained.

EXAMPLE 44

Sodium(2-methyl-3-hydroxy-5-vinyl-4-pyridyl) Methyl Trithiocarbonate

2-Methyl-3-hydroxy-4-chloromethyl-5-vinylpyridine (20 g.) is suspended in water/methanol (100:25 v/v) and treated with disodium trithiocarbonate (33%) (45 g.). The mixture is stirred at 50° C. for 4 hours under nitrogen and adjusted to pH 6.2-6.5 with dilute acid. The precipitate is recrystallized from DMF/water to give sodium(2-methyl-3-hydroxy-5-vinyl-4-pyridyl) methyl trithiocarbonate.

EXAMPLE 45

Bis[2-methyl-3-hydroxy-5-vinylpyridyl-4-methyl] Trithiocarbonate

To a solution of 2-methyl-3-hydroxy-4-chloromethyl-5-vinylpyridine (9 g.) in methanol (100 ml.) is added 22% sodium trithiocarbonate (17.5 ml.) at 20° C. The mixture is kept at 20° C. for 3 hours. The precipitate is collected, washed with water and hot ethanol, and dried and recrystallized from DMF to give bis[2-methyl-3-hydroxy-5-vinylpyridyl-4-methyl]trithiocarbonate.

EXAMPLE 46

2-Methyl-3-Hydroxy-4-Mercaptomethyl-5-Vinylpyridine Hydrochloride

The product from Example 49 (10 g.), methanol, (200 ml.) and 10% NaOH solution (50 ml.) are refluxed for 10 hours. The mixture is neutralized to pH 5-7 with dilute hydrochloric acid, and extracted with ethyl acetate. The extract is concentrated to dryness, and the residue is chromatographed on silica gel by elution with ethyl acetate. The ethyl acetate is concentrated to dryness, the residue is taken up in THF and treated with gaseous hydrogen chloride to precipitate 2-methyl-3-hydroxy-4-mercaptomethyl-5-vinylpyridine hydrochloride.

EXAMPLE 47

S,S'-bis[2-methyl-3-hydroxy-5-vinyl-4-pyridylmethyl]-1,3-Propylenedicarbothioate Employing the procedure of Example 33, but sustituting for the isophthaloyldichloride used therein, an equivlalent amount of glutaroyl chloride, there is produced S,S'-bis[2-methyl-3-hydroxy-5-vinyl-4-pyridylmethyl]-1,3-propylenedicarbothioate.

Similarly, by employing oxalyl chloride, malonoyl chloride, succinoyl chloride or pentane dicarbonyl chloride, there are produced respectively:

S,S'-bis[2-methyl-3-hydroxy-5-vinyl-4-pyridylmethyl]-dicarbothioate.
S,S'-bis[2-methyl-3-hydroxy-5-vinyl-4-pyridylmethyl]-methylenedicarbothioate.
S,S'-bis[2-methyl-3-hydroxy-5-vinyl-4-pyridylmethyl]-1,2-ethylenedicarbothioate, and
S,S'-bis[2-methyl-3-hydroxy-5-vinyl-4-pyridylmethyl]-1,5-pentamethylenedicarbothioate.

EXAMPLE 48

4-Ethoxycarbonylmethylthiomethyl-3-Hydroxy-2-Methyl-5-Vinyl Pyridine

To an ice cold mixture of 0.01 mole of ethylmercapto acetate and 0.02 mole of sodium ethoxide in 100 ml. ethanol under nitrogen is added a solution of 4-bromo-3-hydroxy-2-methyl-5-vinylpyridine hydrobromide in 50 ml. of ethanol. The reaction mixture is stirred overnight at room temperature, concentrated in vacuo and taken up between ethyl acetate and water. The organic layer is separated, washed well with water, dried and concentrated Chromatography of the residue on silica gel-elution with ether-petroleum ether 10-50% gives 4-ethoxycarbonylmethylthiomethyl-3-hydroxy-2-methyl-5-vinyl pyridine.

EXAMPLE 49

4-(2-Amino-2-carboxyethylthiomethyl)-3-Hydroxy-2-Methyl-5-Vinylpyridine

Using 0.01 mole of cysteine and 0.03 moles of sodium methoxide in the procedure of Example 48 gives, after appropriate workup, 4-(2-amino-2-carboxyethylthiomethyl)-3-hydroxy-2-methyl-5-vinylpyridine.

EXAMPLE 50

Bis[2-Methyl-3-Hydroxy-5-Vinylpyridine-4-Methyl]-Disulfide

To a mixture of 0.035 mole of sodium sulfide nonahydrate and 0.034 mole of S in 50 ml. of water is added with stirring 0.02 moles of 4-bromomethyl-3-hydroxy-2-methyl-5-vinylpyridine hydrobromide in 50 ml. $H_2O$. The reaction mixture is stirred overnight and then filtered to isolate crude product and sulfur. The precipitate is extracted with 8% aqueous hydrochloric acid, filtered, and the filtrate then neutralized with sodium bicarbonate. The resulting precipitate is filtered to give bis[2-methyl-3-hydroxy-5-vinylpyridin-4-methyl]disulfide.

EXAMPLE 51

Bis[2-methoxy-3-hydroxy-5-vinylpyridyl-4-methyl]trisulfide

Step A: Preparation of 2-methyl-3-benzyloxy-4-hydroxymethyl-5-vinylpyridine To a mixture of 0.1 mole 3-hydroxy-4-hydroxymethyl-2-methyl-5-vinylpyridine in 500 ml. of acetone and 25 gm. potassium carbonate is added 0.11 mole of benzyl chloride. The reaction mixture is stirred overnight, filtered, and the acetone removed in vacuo to yield 2-methyl-3-benzyloxy-4-hydroxymethyl-5-vinylpyridine.

Step B: Preparation of 2-methyl-3-benzyloxy-4-chloromethyl-5-vinylpyridine

To a solution of 0.1 mole of 3-benzyloxy-4-hydroxymethyl-2-methyl-5-vinylpyridine in 500 ml. of benzene is added dropwise with cooling a solution of 0.11 mole of thionyl chloride in 50 ml. benzene. The reaction mixture is stirred for 1 hour and then filtered to give 2-methyl-3-benzyloxy-4-chloromethyl-5-vinylpyridine.

Step C: Preparation of 2-methyl-3-benzyloxy-4-mercaptomethyl-5-vinylpyridine To a well stirred solution of 0.11 mole of thiourea in 250 ml. methanol, under $N_2$ is added 0.1 mole of 3-benzyloxy-4-chloromethyl-2-methyl-5-vinylpyridine hydrochloride. The mixture is refluxed for 1 hour and then cooled. A solution of 0.4 mole of sodium hydroxide in 50 ml. of water is added, and the resulting mixture refluxed for 30 minutes. After concentration in vacuo the reaction mixture is taken up between benzene and water and enough acetic acid added to neutralize the mixture. The organic layer is separated, washed well with water, dried, and concentrated to give 2-methyl-3 1 -benzyloxy-4-mercaptomethyl-5-vinylpyridine.

Step D: Preparation of bis[2-methyl-3-benzyloxy-5-vinylpyridyl-4-methyl]trisulfide To 0.01 mole of sodium hydride in 50 ml. dry dimethylformamide under nitrogen at 0° 14 5° is added 0.01 mole of 2-methyl-3-benzyloxy-4-mercaptomethyl-5-vinylpyridine in 10 ml. of dimethylformamide. When the evolution of hydrogen has ceased, 0.005 mole of sulfur dichloride is added. The reaction mixture is stirred overnight, poured into benzene-ice water, dried and concentrated. Chromatography on silica gel and elution with ether-petroleum ether (10–80%) gives bis[2-methyl-3-benzyloxy-5-vinylpyridyl-4-methyl]trisulfide.

Step E: Preparation of bis[2-methoxy-3-hydroxy-5-vinylpyridyl-4-methyl]trisulfide A mixture of 0.01 mole bis(3-benzyloxy-2-methyl-5-vinylpyridyl-4-methyl)trisulfide in 10 ml. concentrated hydrochloric acid and 20 ml. acetic acid is heated 2 hours at 60°. The reaction mixture is concentrated in vacuo and taken up between benzene-ether (1:1) and saturated sodium bicarbonate solution. The organic layer is separated, washed with water, dried and concentrated in vacuo to yield bis[2-methoxy-3-hydroxy-5-vinylpyridyl-4-methyl]trisulfide.

EXAMPLE 52

Bis [2-Methyl-3-Hydroxy-5-Vinylpyridyl-4-Methyl]Tetrasulfide

Following the procedure substantially as described in Example 51, Steps D and E, but substituting for the sulfur dichloride used in Step D, an equimolar amount of sulfur monochloride, there is produced in turn, bis[2-methyl-3-benzyloxy-5-vinylpyridyl-4-methyl]tetrasulfide and bis[2-methyl-3-hydroxy-5-vinylpyridyl-4-methyl]tetrasulfide.

EXAMPLE 53

Bis [2-Methyl-3-Hydroxy-5-Vinylpyridyl-4-Methyl]Disulfide

Step A: Preparation of 2,2,8-trimethyl-4H-m-dioxino-[4,5-C]pyridine-5-methanol Materials:
1700 ml. acetone
500 gm. pyridoxine hydrochloride
~825 gm. anhydrous hydrogen chloride
2360 gm. 50% w/w sodium hydroxide solution Into a 5 liter, 3-necked flask fitted with a thermometer, stirrer, and gas inlet tube was charged 500 gm. (2.43 moles) of pyridoxine hydrochloride and 1400 ml. of acetone. The slurry was cooled to 0°–5° and anhydrous hydrogen chloride added at this temperature until a clear pale yellow solution resulted. Aged at this temperature for 1 hour.

After aging at 0°–5° for 1 hour, the solution was slowly added to an efficiently cooled and agitated mixture of 2360 gm. of 50% w/w NaOH (29.5 moles) and 3 liters of water holding the temperature below 35°.

The resulting white slurry was cooled to 20°, filtered and washed with 5 × 100 ml. of water. Air drying over the weekend gave 472 gm. of product melting at 90°–94°. Washing on a funnel with acetone gave 398 gm. of product melting at 90°–101° when air dried and 361 gm. (71%) melting at 108°–100° when dried at 45° under vacuum.

The mother liquors from the first filtration, on standing overnight, produced 53 gm. of product which melted at 108°–110° when dried at 45° under vacuum. The total yield thus was 414 gm. of 81%.

Step B: Preparation of 5-formyl-2,2,8-trimethyl-4H-m-dioxino[4,5-c]pyridine

Materials:
125.4 gm. 2,2,8-trimethyl-4-H-m-dioxino[4,5-c]pyridine-5-methanol
2400 ml. benzene
250.8 gm. MnO$_2$ ("Activated")
300 ml. hexane A three liter, three-necked flask was set up, equipped with an agitator, thermometer, Dean-Stark trap and condenser. To this was charged 1650 ml. of benzene and 250.8 gm. of MnO$_2$. The mixture was refluxed 1-½ hours during which time a total of 3.0 ml. of water was removed from the trap. The mixture was cooled to 30° and 125.4 gm. (0.600 moles) of 2,2,8-trimethyl-4H-m-dioxino[4,5-c]pyridine-5-methanol from Step A added.

Again the mixture was refluxed drawing off 4.8 ml. (0.266 moles) of water over 2 hours.

The black slurry was cooled to 25° and filtered. The resulting cake was washed with 3 × 250 ml. of benzene. The filtrate and washings were stripped to a volume of 150–200 ml. under vacuum, 200 ml. of hexane added and again vacuum stripped to a volume of 150–200 ml. An additional 100 ml. of hexane was added and the slurry cooled to 0°–5° and aged 1 hour.

The product was filtered and washed with 1 × 50 ml. of hexane. It was dried overnight at room temperature under vacuum to give 81.60 gm. (65.6%), m.p. 61.5°–64°.

The mother liquor was stripped to a dry solid (constant weight) under vacuum to yield 24.10 gm. (19.4%), m.p. 56°–60°. Total yield 85%.

Step C: Preparation of methyltriphenylphosphonium bromide

Materials:
492 gm. triphenyl phosphine
249 gm. methyl bromide
3000 ml. benzene

To a four liter Erlenmeyer flask was charged 492 gm. of triphenyl phosphine and 1200 ml. of benzene. The mixture was stirred magnetically for ten minutes until a clear solution resulted. Methyl bromide (249 gm.) chilled to −10° was added and the flask stoppered and taped shut. The mixture was stirred overnight at room temperature.

An additional 900 ml. of benzene was added and the mixture heated to 50° while breaking up lumps. The slurry was cooled to 30°, filtered and washed with 3 × 300 ml. of benzene.

The product was dried to constant weight at 50°–55° under vacuum.

The yield was 662 gm. (98.8%), m.p. 228°–230°.

Step D: Preparation of 5-ethenyl-3-hydroxy-2-methyl-4-pyridine methanol

Materials:
10 liters tetrahydrofuran
1455 gm. methyl triphenylphosphonium bromide
2.31 liters 1.6 M butyl lithium (in hexane)
763 gm. 5-formyl-2,2,8-trimethyl-4H-m-dioxino-[4,5-c]pyridine
12 liters benzene
185 gm. sodium bisulfite
116 ml. ethanol
6.83 liters 2.5 N hydrochloric acid (1.48 liters conc. HCl + 5.35 l water)
850 ml. 50% w/w sodium hydroxide (aq.)

To a 20 liter, 3-necked flask equipped with an agitator, thermometer, nitrogen inlet, dropping funnel and drying tube was charged 8.75 liters of tetrahydrofuran and 1,455 gm. (4.06 moles) of methyl triphenylphosphonium bromide.

Butyl lithium solution (2.31 liters of 1.6 M = 3.69 moles) in hexane was added over 45 minutes maintaining 25° with an ice bath. The thin yellow slurry was aged for 1.5 hours.

5-Formyl-2,2,8-trimethyl-4-H-m-dioxino[4,5-c]-pyridine (763 gm. = 3.69 moles) was dissolved in 1940 ml. of dry tetrahydrofuran and a small amount of insoluble material filtered out.

The THF solution of the aldehyde was charged to the batch over 1 hour maintaining the temperature at 25° with an ice-bath and the resulting deep yellow slurry aged with stirring for 1 hour.

After aging, the reaction mixture was quenched into a stirred mixture of 7.75 liters of water and 7.75 liters of benzene and stirred approximately 30 minutes or until two clear layers resulted. The water layer was discarded and the organic layer extracted with 7.75 liters of water which was also discarded. The organic layer was now extracted with a solution of 185 gm. of sodium bisulfite dissolved in 384 ml. of water to which 116 ml. of ethanol had been added when the salt dissolved. The bisulfite extract was also discarded.

The organic layer was extracted with 6.8 liters of 2.5 N hydrochloric acid and then the water layer back washed with 2.1 liters of benzene.

The acid solution of product was subject to approximately 28 inches vacuum and the temperature gradually raised to 35° during which time residual solvents were removed and finally water began to distill. Under atmospheric pressure, the temperature of the solution was raised to 90°, held for 20 minutes, then cooled rapidly to 15°.

To the batch was added 1,330 ml. of THF and the solution slowly neutralized to pH 4.7 ± 0.2 over a 1 hour period with approximately 850 ml. of 50% w/w sodium hydroxide solution holding the temperature at 25°. The batch was seeded with 100 mg. of product and stirred 1.5 hours until crystallization was well under way. The pH of the mixture was now carefully raised over 1 hour with approximately 70 ml. of 50% sodium hydroxide to pH 7.0 ± 0.2. The slurry was aged overnight with stirring at 25°.

The product was filtered and washed with 3 × 370 ml. of water. It was air dried at 25° to a constant weight of 490 gm. (80.6%), melting point 162°–167.5° (d).

Step E: Preparation of 4,4'-dithiodimethylenebis(5-ethenyl-2-methyl-3-pyridinol)

Materials:
485 gm. 5-ethenyl-3-hydroxy-2-methyl-4-pyridine methanol
7 liters ethanol-2BA 517 gm. sodium hydroxide pellets reagent grade
590 ml. carbon disulfide
990 ml. conc. hydrochloric acid
4.5 liters ethyl acetate
~150 ml. 50% sodium hydroxide solution
6.6 liters 2.5% sodium hydroxide solution
140 ml. 30% hydrogen peroxide
~390 ml. 1:1 hydrochloric acid A 12 liter, 3-necked flask was set up and equipped with an agitator, thermometer, condenser, dropping funnel and nitrogen inlet. To this was charged 5.15 liters of ethanol-2BA and 517 gm. (12.9 moles) of sodium hydroxide pellets. The mixture was allowed to warm to 50° to aid solution and, when solution was complete, cooled to 25°.

To this solution was added 485 gm. (2.93 moles) of 5-ethenyl-3-hydroxy-2-methyl-4-pyridine methanol. The solution was cooled at 10°-15° and 295 ml. (4.85 moles) of carbon disulfide added over 30 minutes at 10°-15°. The batch was warmed to 25° and aged 30 minutes. The mixture was again cooled to 10°-15° and an additional 295 ml. of carbon disulfide added over 30 minutes at that temperature. The batch was then warmed to 25° and held 1 hour.

The reaction mixture was carefully heated to reflux over 1 hour and held at reflux for 1 hour. It was then cooled to 25°, 200 gm. of Supercel was added, and the solids removed by filtration through two 6 inches funnels precoated with 50 gm. each of Supercel. The cakes were washed with a total of 1500 ml. of ethanol-2BA.

The clear filtrate was concentrated under vacuum at a maximum batch temperature of 30° to a volume of 2 to 2.5 liters. Four liters of water was added and at 5°-10° the pH adjusted to 2 ± 0.2 with approximately 975 ml. of concentrated hydrochloric acid. Vacuum stripping was continued until a clear solution was obtained and then for an additional thirty minutes.

To the clear solution was added 3 liters of ethyl acetate and the pH adjusted to 7 ± 0.2 by the addition of approximately 150 ml. of 50% sodium hydroxide with stirring at 20°-25°. The layers were separated and held. The aqueous layer was extracted a second time with 1.5 liters of ethyl acetate, the layers separated, and the ethyl acetate layers combined.

The combined ethyl acetate solution was extracted with 1 × 590 ml. of 2.5% sodium hydroxide solution.

The clear combined aqueous extracts were cooled to 5°-10° and 140 ml. of 30% hydrogen peroxide carefully added over 30-45 minutes.

The reaction mixture was warmed carefully to 25° and aged at this temperature for 1 hour. Ethanol (2.5 liters) was added and the pH adjusted to 7 ± 0.2 with approximately 390 ml. of 1:1 hydrochloric acid. The slurry was aged 30 minutes and filtered. The cake was washed with a total of 1.5 liters of 1:1 ethanol-water. The product was air dried at 25° to a constant weight. Yield 427 gm. (73.3%, calculated as dihydrate), m.p. = 190°-193°.

Step F: Preparation of 4,4'-dithiodimethylenebis(5-ethenyl-2-methyl-3-pyridinol)sulfate monohydrate In a 12 liter flask, 259 gm. of concentrated sulfuric acid (Baker Analyzed, 95.6%) was added to 4.25 liters of water and heated to 70°. To this was added 425 gm. of the crude free base from the previous step (Run No. 8145-259-3) and the slurry heated to 90° where solution took place. The orange colored solution was treated with 42.5 gm. of Nuchar C-190N, aged 5 minutes at 90°-93° and filtered through a layer of 50 gm. of Supercel. The cake was washed with 2 × 100 ml. of hot 1 N $H_2SO_4$ solution.

The somewhat lighter colored solution was cooled immediately to room temperature and finally to 0°-5° where it was aged with stirring for 1 hour.

The product was filtered, washed with 1 × 120 ml. of distilled water, slurried on the funnel with 1 × 200 ml. of water, and finally washed with 1 × 120 ml. of water. The product was dried under vacuum at 25° to constant weight. The yield was 427 gm. (83.5%); m.p. 157.5° C. (dec.).

Analytical data:
Color: Pale light yellow
M.P.: 157.5° (decomposition)
$UV_{303}$: 351* (N/10 HCl)
TGA to 120°: 4.4% (Theory = 3.85%)
Elemental Anal.:
Calculated for $C_{18}H_{20}N_2O_2S_2 \cdot H_2SO_4 \cdot H_2O$

| | Calculated | Found* |
|---|---|---|
| C | 45.35 | 45.25 |
| H | 5.08 | 5.21 |
| N | 5.89 | 5.64 |

LC: 99.4 ± 1.0%*
TLC: One impurity and streaking (Analtech GF/16:8:1 Spotted from 2N HCl/THF)
ROI: 0.02%
HM: <10 PPM

*Uncorrected for the 0.55% TGA over theory.

Step G: Preparation of 4,4'-dithiodimethylenebis(5-ethenyl-2-methyl-3-pyridinol) (free base)

A run according to that described in Step F was made using 12.0 gm. of crude disulfide. The yield of damp cake was 17.86 gm.

A solution of 5.6 gm. of sodium bicarbonate was made in 120 ml. of water and 120 ml. of ethanol added. By warming to 50° precipitated bicarbonate redissolved.

The damp cake from above was added to the bicarbonate solution as fast as evolved carbon dioxide would allow (30 minutes) and the resulting slurry stirred at 50° for 1 hour. The slurry was cooled to room temperature and stirred 1 hour.

The slurry was filtered and washed with 3 × 10 ml. of water (Sulfate ion test slightly positive). After washing with an additional 1 × 10 ml. of water (test negative), the product was dried in a vacuum (1 mm) desiccator overnight at room temperature to constant weight.

The overall yield was 10.81 gm. (90%) of dihydrate; m.p. 197°-198° C. (dec.).

EXAMPLE 54

A mixture of 250 parts of 2-methyl-3-hydroxy-4-mercaptomethyl-5-vinylpyridine hydrochloride and 25 parts of lactose is granulated with suitable water, and to this is added 100 parts of maize starch. The mass is passed through a 16 mesh screen. The granules are dried at a temperature below 60° C. The dry granules are passed through a 16 mesh screen, and mixed with 3.8 parts of magnesium stearate. They are then compressed into tablets suitable for oral administration.

The specific mercaptomethylpyridine used in the foregoing example may be replaced by 25, 100, 250, or 500 parts of other mercaptoalkylpyridines of this invention to produce tablets suitable for oral administration according to the method of this invention.

EXAMPLE 55

A mixture of 50 parts of 2-methyl-3-hydroxy-4-mercaptomethyl-5-vinylpyridine hydrochloride, 3 parts of the calcium salt of lignin sulfonic acid, and 237 parts of water is ball-milled until the size of substantially all of the particles is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

EXAMPLE 56

A mixture of 250 parts of 2-methyl-3-hydroxy-4-vinyl-5-mercaptomethylpyridine, 200 parts of maize starch, and 30 parts of alginic acid is mixed with a sufficient quantity of 10% aqueous paste of maize starch, and granulated. The granules are dried in a current of warm air, and the dry granules are then passed through a 16-mesh screen, mixed with 6 parts of magnesium stearate and compressed into tablet form to obtain tablets suitable for oral administration.

EXAMPLE 57

A mixture of 500 parts 2-methyl-3-hydroxy-4-mercaptomethyl-5-ethynylpyridine, 60 parts maize starch, and 20 parts of gum acacia is granulated with a sufficient quantity of water. The mass is passed through a 12-mesh screen, and the granules are dried in a current of warm air. The dry granules are passed through a 16-mesh screen, mixed with 5 parts of magnesium stearate and compressed into tablet form suitable for oral administration.

EXAMPLE 58

1. Tablets — 10,000 scored tablets for oral use, each containing 500 mg. of active ingredient are prepared from the following ingredients:

|  | Gm. |
|---|---|
| 2-methyl-3-hydroxy-4-mercapto-methyl-5-(1-propenyl)pyridine hydrochloride | 5000 |
| Starch, U.S.P. | 350 |
| Talc, U.S.P. | 250 |
| Calcium stearate | 35 |

The powdered mercaptomethylpyridine is granulated with a 4% w./v. aqueous solution of methylcellulose U.S.P. (1500 cps.). To the dried granules is added a mixture of the remainder of the ingredients and the final mixture compressed into tablets of proper weight.

2. Capsules — 10,000 two-piece hard gelatine capsules for oral use, each containing 250 mg. of active ingredient are prepared from the following ingredients:

|  | Gm. |
|---|---|
| 2-methyl-3-hydroxy-4-mercapto-methylpyridine-5-acrylic acid | 2500 |
| Lactose, U.S.P. | 1000 |
| Starch, U.S.P. | 300 |
| Talc, U.S.P. | 65 |
| Calcium stearate | 25 |

The powdered mercaptomethyl compound is mixed with the starch-lactose mixture followed by the talc and calcium stearate. The final mixture is then encapsulated in the usual manner. Capsules containing 10, 25, 50, and 100 mg. of active ingredient are also prepared by substituting 100, 250, 500, and 1000 gm. for 2500 gm. in the above formulation.

3. Soft elastic capsules — One-piece soft elastic capsules for oral use, each containing 500 mg. of active material are prepared in the usual manner by first dispersing the powdered active material in sufficient corn oil to render the material capsulatable.

4. Aqueous suspension — An aqueous suspension for oral use containing in each 5 ml., 1 gm. of active ingredient is prepared from the following ingredients:

|  | Gm. |
|---|---|
| 3-o-4α-S-benzylidine derivative of 2-methyl-3-hydroxy-4-mercaptomethyl-5-vinylpyridine | 2000 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D.&C. orange dye | 7.5 |
| Deionized water, q.s. to 10,000 ml. |  |

What is claimed is:

1. A compound of structural formula:

$$\begin{array}{c} R^1 \\ | \\ R^2-C-SH \\ R''O \diagdown \diagup \\ \diagdown \diagup A-R^4 \\ R \diagup \diagdown N \diagup \\ \downarrow \\ (O)_m \end{array}$$

or pharmaceutically acceptable salt thereof wherein
m is 0 or 1;
R" is H or $C_{2-6}$ alkanoyl;
A is $$-CH=C \atop | \atop R^7$$

or $-C\equiv C-$
where $R^7$ is hydrogen, chloro or fluoro;
R is $C_{1-3}$ alkyl, hydroxy, $C_{2-6}$ alkanoyloxy, or hydroxy - $C_{1-3}$ alkyl;
$R^1$ and $R^2$ are hydrogen or $C_1 - _3$ alkyl; and
$R^4$ is hydrogen, $C_{1-3}$ alkyl, phenyl, chloro, fluoro, or carboxyl.

2. 2-Methyl-3-hydroxy-4-mercaptomethyl-5-vinylpyridine or pharmaceutically acceptable salt thereof.

3. 2-Methyl-3-hydroxy-4-mercaptomethylpyridine-5-acrylic acid or a pharmaceutically acceptable salt thereof.

4. 2-Methyl-3-hydroxy-4-mercaptomethyl-5-(1-propenyl)pyridine or a pharmaceutically acceptable salt thereof.

5. 2-Methyl-3-hydroxy-4-mercaptomethyl-5-ethynylpyridine or a pharmaceutically acceptable salt thereof.

6. 2-Methyl-3-hydroxy-4-mercaptomethyl-5-styrylpyridine or pharmaceutically acceptable salt thereof.

7. The compound of claim 1 of structural formula:

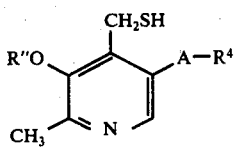

wherein R", A, and R⁴ have the same meaning as set forth in said claim.

8. An anti-inflammatory composition in unit dosage form comprising a pharmaceutically acceptable inert carrier and from 5 mg. to 5 gm. of a compound of structural formual:

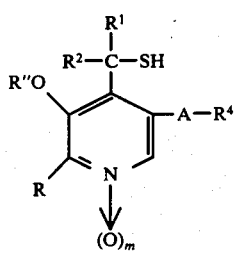

or pharmaceutically acceptable salt thereof wherein
m is 0 or 1;
R" is H or $C_{2-6}$ alkanoyl;
A is

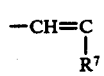

or —C≡C—
where $R^7$ is hydrogen, chloro or fluoro;
R is $C_{1-3}$ alkyl, hydroxy, $C_{2-6}$ alkanoyloxy, or hydroxy - $C_{1-3}$ alkyl;
$R^1$ and $R^2$ are hydrogen or $C_{1-3}$ alkyl; and
$R^4$ is hydrogen, $C_{1-3}$ alkyl, phenyl, chloro, fluoro, or carboxyl.

9. The anti-inflammatory composition of claim 8 wherein the active ingredient is a compound of structural formula:

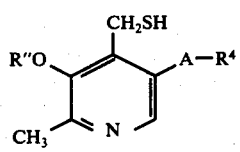

wherein R", A and R⁴ have the same meaning as set forth in said claim.

10. The anti-inflammatory composition of claim 9 wherein the compound is 2-methyl-3-hydroxy-4-mercaptomethy-5-vinylpyridine or pharmaceutically accpetable salt thereof.

11. The anti-inflammatory composition of claim 9 wherein the compound is 2-methyl-3-hydroxy-4-mercaptomethylpyridine-5-acrylic acid or pharmaceutically acceptable salt thereof.

12. The anti-inflammatory composition of claim 9 wherein the compound is 2-methyl-3-hydroxy-4-mercaptomethyl-5-(1-propenyl) pyridine or pharmaceutically acceptable salt thereof.

13. The anti-inflammatory composition of claim 9 wherein the compound is 2-methyl-3-hydroxy-4-mercaptomethyl-5-ethynylpyridine or pharmaceutically acceptable salt thereof.

14. The anti-inflammatory composition of claim 9 wherein the compound is 2-methyl-3-hydroxy-4-mercaptomethyl-5-styrylpyridine or pharmaceutically accpetable salt thereof.

15. A method of treating rheumatoid arthritis which comprises the administration, to a warm-blooded animal or human in need of such treatment, an effective amount of a compound of structural formula:

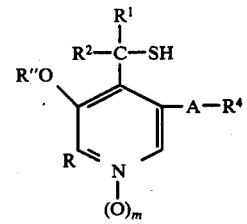

or pharmaceutically acceptable salt thereof wherein
m is 0 or 1;
R" is H or $C_{2-6}$ alkanoyl;
A is

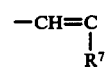

or — C≡C—
where $R^7$ is hydrogen, chloro or fluoro;
R is $C_{1-3}$ alkyl, hydroxy, $C_{2-6}$ alkanoyloxy, or hydroxy - $C_{1-3}$ alkyl;
$R^1$ and $R^2$ are hydrogen as $C_{1-3}$ alkyl; and
$R^4$ is hydrogen, $C_{1-3}$ alkyl, phenyl, chloro, fluoro, or carboxyl.

16. The method of claim 15 wherein the compound is of structural formula:

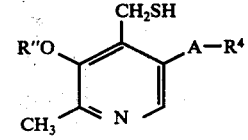

wherein R", A, and R⁴ have the same meaning as set forth in said claim.

17. The method of claim 16 wherein the compound is 2-methyl-3-hydroxy-4-mercaptomethyl-5-vinylpyridine or pharmaceutically acceptable salt thereof.

18. The method of claim 16 wherein the compound is 2-methyl-3-hydroxy-4-mercaptomethylpyridine-5-acrylic acid or pharmaceutically acceptable salt thereof.

19. The method of claim 16 wherein the compound is 2-methyl-3-hydroxy-4-mercaptomethy-5-(1-propenyl) pyridine or pharmaceutically acceptable salt thereof.

20. The method of claim 16 wherein the compound is 2-methyl-3-hydroxy-4-mercaptomethyl-5-ethynylpyridine or pharmaceutically acceptable salt thereof.

21. The method of claim 16 wherein the compound is 2-methyl-3-hydroxy-4-mercaptomethyl-5-styrylpyridine or pharmaceutically acceptable salt thereof.

* * * * *